US006413920B1

(12) United States Patent
Bettiol et al.

(10) Patent No.: US 6,413,920 B1
(45) Date of Patent: Jul. 2, 2002

(54) AMINE REACTION COMPOUNDS COMPRISING ONE OR MORE ACTIVE INGREDIENT

(75) Inventors: Jean-Luc Philippe Bettiol, Brussels; Alfred Busch, Londerzeel; Hugo Denutte, Hofstade; Christophe Laudamiel, Brussels; Peter Marie Kamiel Perneel, Brugge; Marie Montserrat Sanchez-Pena, Brussels; Johan Smets, Lubbeek, all of (BE)

(73) Assignee: Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/720,395

(22) PCT Filed: Jul. 12, 1999

(86) PCT No.: PCT/US99/15665

§ 371 (c)(1),
(2), (4) Date: Dec. 20, 2000

(87) PCT Pub. No.: WO00/02991

PCT Pub. Date: Jan. 20, 2000

(30) Foreign Application Priority Data

Jul. 10, 1998 (EP) ........................................ 98870156
Oct. 28, 1998 (EP) ........................................ 98870227

(51) Int. Cl.[7] ........................ C11D 7/32; C11D 3/50; C11D 3/37; C07D 295/13

(52) U.S. Cl. ........................ 510/101; 510/475; 512/1; 525/417

(58) Field of Search ........................ 510/101, 102, 510/475; 512/7; 525/417

(56) References Cited

U.S. PATENT DOCUMENTS

| | | | | | |
|---|---|---|---|---|---|
| 3,625,710 | A | | 12/1971 | Rizzi | 99/140 |
| 4,853,369 | A | | 8/1989 | Mookherjee et al. | 512/25 |
| 5,188,753 | A | | 2/1993 | Schmidt et al. | 252/132 |
| 5,270,379 | A | | 12/1993 | McAndrew et al. | 524/555 |
| H1468 | H | | 8/1995 | Costa | 252/174.12 |
| 5,643,498 | A | * | 7/1997 | Li et al. | 252/357 |

FOREIGN PATENT DOCUMENTS

| | | |
|---|---|---|
| DE | 17 95 617 | 3/1972 |
| DE | 011 499 | 5/1980 |
| DE | 175871 | 4/1986 |
| DE | 392619 | 10/1990 |
| DE | 831143 | 3/1998 |
| EP | 841391 | 5/1998 |
| JP | 09040687 | 2/1997 |
| WO | WO 93/19787 | 10/1993 |
| WO | WO 95/04809 | 2/1995 |
| WO | WO 95/08976 | 4/1995 |
| WO | WO 96/38528 | 12/1996 |

OTHER PUBLICATIONS

Kamogawa et al., Chemical Release Control—Schiff Bases Of Perfume Aldehydesand Aminostyrenes, Journal of Polymer Science: Polymer Chemistry Edition, vol. 20, 1982, pp 3132–3129.

Viguera et al., A Water–Soluble Polylysine–Retinaldehyde Schiff Base Stability in Aqueous And Nonaqueous Environments, Journal of Biological Chemistry, vol. 265, No. 5, 2/15/90 pp 2527–2532 (XP002057413/ISSN:0021–9258).

* cited by examiner

*Primary Examiner*—John Hardee
(74) *Attorney, Agent, or Firm*—Richard S. Echler, Sr.; Kim W. Zerby; Steve W. Miller

(57) ABSTRACT

The present invention relates to a product of reaction between a primary and/or secondary amine and one or more active ingredients. By the present invention, there is provided a release of the active component over a longer period of time than by the use of the active itself.

13 Claims, No Drawings

AMINE REACTION COMPOUNDS COMPRISING ONE OR MORE ACTIVE INGREDIENT

FIELD OF THE INVENTION

The present invention relates to product of reaction between an amine and an active component, in particular an active aldehyde or ketone, more preferably an aldehyde or ketone perfume. More particularly, it relates to such product of reaction for use in softening compositions.

BACKGROUND OF THE INVENTION

Perfumed products are well-known in the art. However, consumer acceptance of such perfumed products like softening products is determined not only by the performance achieved with these products but also by the aesthetics associated therewith. The perfume components are therefore an important aspect of the successful formulation of such commercial products.

It is also desired by consumers for treated fabrics to maintain the pleasing fragrance over time. Indeed, perfume additives make such compositions more aesthetically pleasing to the consumer, and in some cases the perfume imparts a pleasant fragrance to fabrics treated therewith. However, the amount of perfume carried-over from an aqueous laundry bath onto fabrics is often marginal and does not last long on the fabric. Furthermore, fragrance materials are often very costly and their inefficient use in laundry and cleaning compositions and ineffective delivery to fabrics results in a very high cost to both consumers and laundry and cleaning manufacturers. Industry, therefore, continues to seek with urgency for more efficient and effective fragrance delivery in laundry and cleaning products, especially for improvement in the provision of long-lasting fragrance to the fabrics.

One solution is to use carrier mechanisms for perfume delivery, such as by encapsulation. This is taught in the prior art and described in U.S. Pat. No. 5,188,753.

Still another solution is to formulate compounds which provide a delayed release of the perfume over a longer period of time than by the use of the perfume itself. Disclosure of such compounds may be found in WO 95/04809, WO 95/08976 and co-pending application EP 95303762.9.

However, notwithstanding the advances in the art, there is still a need for a compound which provides a delayed release of the active component, in particular a perfume ingredient.

That need is even more acute for perfume ingredients which are characteristic of the fresh notes, namely the aldehydes and ketones perfume ingredients. Indeed, whilst these provide a fresh fragrance, these perfumes are also very volatile and have a low substantivity on the surface to be treated like fabrics.

Accordingly, it is a further object of the invention to provide a softening composition comprising a perfume component which provides a fresh fragrance and is substantive to the treated surface.

The Applicant has now found that specific reaction products of amine compounds with an active aldehyde or ketone, such as imines compounds, also provide a delayed release of the active such as a perfume.

Imine compounds are known in the art under the name of Schiff bases which is the condensation of an aldehyde perfume ingredient with an anthranilate. A typical description can be found in U.S. Pat. No. 4,853,369. By means of this compound, the aldehyde perfume is made substantive to the fabrics. However, a problem encountered with these Schiff bases is that the methylanthranilate compound also exhibits a strong scent, which as a result produces a mixture of fragrances, thereby reducing or even inhibiting the aldehyde and/or ketone fragrance perception.

To achieve such perfume composition with comparable aldehyde or ketones fresh notes whilst still having satisfactory fabric substantivity, perfumers have formulated around the composition. For example, by having a carrier or encapsulating material for such notes such as with cyclodextrin, zeolites or starch.

Still another solution is the use of a glucosamine as described in JP 09040687. However, this compound has been found to give a very low stability in the wash process. As a result, insufficient perfume residuality on the treated fabric has been found with these glucosamine compounds. Its use in softening composition is not disclosed.

A further solution is described in Chemical release control, Kamogawa et Al., J. Poly. Sci. . Polym. Chem. Ed. Vol 20, 3121 (1982) which describe the use of amino styrene compounds condensed with aldehydes perfumes, whereby the release of the perfume is triggered by means of copolymerisation or acidification of the compound. Its application is however not mentioned.

The Applicant has now found that a reaction product between a specific primary and/or secondary amine and an active component also fulfill such a need.

Another advantage of the compounds of the invention is their ease of manufacture rendering their use most desirable.

SUMMARY OF THE INVENTION

The present invention relates to product of reaction between a primary and/or secondary amine compound and an active component selected from ketone, aldehyde, and mixtures thereof, characterised in that said amine compound has an Odor Intensity Index of less than that of a 1% solution of methylanthranilate in dipropylene glycol, Dry Surface Odor Index of more than 5; and with the proviso that said amine compound is not an aminostyrene.

In another aspect of the invention, there is provided a softening composition comprising a primary and/or secondary amine compound and an active component selected from ketone, aldehyde, and mixtures thereof, characterised in that said amine compound has an Odor Intensity Index of less than that of a 1% solution of methylanthranilate in dipropylene glycol.

In a further aspect of the invention, there is provided a method of delivering residual fragrance to a surface which comprises the steps of contacting said surface with a compound or composition of the invention and thereafter contacting the treated fabric with a material so that the active is released from the reaction product between the amine and the active.

DETAILED DESCRIPTION OF THE INVENTION

The essential component of the invention is the product of reaction between a primary and/or secondary amine compound and an active component selected from ketone, aldehyde, and mixtures thereof, characterised in that said amine compound has an Odor Intensity Index of less than that of a 1% solution of methylanthranilate in dipropylene glycol, Dry Surface Odor Index of more than 5; and with the proviso that said amine compound is not an aminostyrene.

When incorporated in softening compositions, the amine reaction product is a product of reaction between a primary and/or secondary amine compound and an active component selected from ketone, aldehyde, and mixtures thereof, characterised in that said amine compound has an Odor Intensity Index of less than that of a 1% solution of methylanthranilate in dipropylene glycol.

Preferably, this compound has a Dry Surface Odor Index of more than 5.

I-Product of Reaction Between a Compound Containing a Primary and/or Secondary Amine Functional Group and a Perfume Component An essential component of the invention is a product of reaction between a compound containing a primary and/or secondary amine functional group and a perfume component, so called hereinafter “amine reaction product”.

A-Primary and/or Secondary Amine

By “primary and/or secondary amine”, it is meant a compound which carries at least one primary and/or secondary amine and/or amide function.

The primary and/or secondary amine compound is also characterized by an Odor Intensity Index of less than that of a 1% solution of methylanthranilate in dipropylene glycol.

Odor Intensity Index Method

By Odor Intensity Index, it meant that the pure chemicals were diluted at 1% in Dipropylene Glycol, odor-free solvent used in perfumery. This percentage is more representative of usage levels. Smelling strips, or so called “blotters”, were dipped and presented to the expert panellist for evaluation. Expert panellists are assessors trained for at least six months in odor grading and whose gradings are checked for accuracy and reproducibility versus a reference on an on-going basis. For each amine compound, the panellist was presented two blotters: one reference (Me Anthranilate, unknown from the panellist) and the sample. The panellist was asked to rank both smelling strips on the 0–5 odor intensity scale, 0 being no odor detected, 5 being very strong odor present.

Results

The following represents the Odor Intensity Index of an amine compound suitable for use in the present invention and according to the above procedure. In each case, numbers are arithmetic averages among 5 expert panellists and the results are statistically significantly different at 95% confidence level:

Methylanthranilate 1% (reference) 3.4

Ethyl-4-aminobenzoate (EAB) 1% 0.9

A general structure for the primary amine compound of the invention is as follows:

$B—(NH2)_n$;

wherein B is a carrier material, and n is an index of value of at least 1.

Compounds containing a secondary amine group have a structure similar to the above excepted that the compound comprises one or more —NH— groups instead of —NH2. Further, the compound structure may also have one or more of both —NH2 and —NH— groups.

Preferred B carriers are inorganic or organic carriers.

By “inorganic carrier”, it is meant a carrier which is non-or substantially non carbon based backbones.

Among the inorganic carriers, preferred inorganic carriers are mono or polymers or organic-organosilicon copolymers of amino derivatised organo silane, siloxane, silazane, alumane, aluminum siloxane, or aluminum silicate compounds. Typical examples of such carriers are: organosiloxanes with at least one primary amine moiety like the diaminoalkylsiloxane [H2NCH2(CH3) 2Si]O, or the organoaminosilane (C6H5) 3SiNH2 described in: Chemistry and Technology of Silicone, W. Noll, Academic Press Inc. 1998, London, pp 209, 106).

Mono or polymer or organic-organosilicon copolymers containing one or more organosilylhydrasine moiety are also preferred. A typical example of such a class of carrier material is the N,N'-bis(trimethylsilyl)hydrazine (Me3Si) 2NNH2 described in: The OrganoSilicon Chemistry Second international Symposium, Pure and Applied Chemistry, Vol, 19 Nos 3–4, (1969).

The following are also preferred mono or poly silazanes and which are exemplified by the 1,1,1,3,3,3,-hexamethyl-2-phenyidiaminosilyldisilasane [(CH3) 3Si] 2NSi(C6H5) NH2) 2 described in: OrganoSilicon Compounds, 1965, V. Bazant and al. Academic Press). Still other preferred examples of polymer silicone derivatives are the cyclic 1,1,5,5,7,7,711,11-Octamethyl-3-9-bis-[2-(2-aminoethylamino)-ethyl]-1,5,7,11-tetrasila-3,9-diaza-6,12-dioxacyclododecane and the Hexaethoxydiamino cyclotetrasiloxane (C6H5) (NH2) 2Si4O4, id, Vol 2 part 2, p 474, p454).

Preferred amino functionalized inorganic polymeric carriers for use herein are polyaminoalkyl polysiloxanes. Typical disclosure can be found in JP 79,131,096, and EP 058 493. Still other inorganic polymeric carriers suitable for use herein are the amino functionalized polydi-alkylsiloxanes, as described in EP 150 867 and having the general formula:

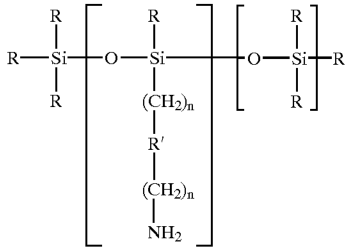

Wherein R=$C_{1-16}$ preferentially $C_{1-4}$ alkyl; n is an integer from 0 to 16 preferentially from 1 to 6, R'=nil, O, C=O, COO, NC=O, C=O—NR, NR, $SO_m$, m=2,3.

By organic carriers, it meant carriers having essentially carbon bond backbones. Typical amines having organic carrier include aminoaryl derivatives, polyamines, aminoacids and derivatives, substituted amines and amides, glucamines, dendrimers and amino-substitued mono-, di-, oligo-, poly-saccharides.

Of course, the amine compound can be interrupted or substituted by linkers or cellulose substantive group. A general formula for this amine compound may be represented as follows:

$NH2_n—L_m—B—L_m—R^*_m$;

wherein each m is an index of value 0 or at least 1, and n is an index of value of at least 1 as defined herein before. As can be seen above, the amine group is linked to a carrier molecule as defined by classes hereinafter described. The primary and/or secondary amine group is either directly linked to the carrier group or via a linker group L. The carrier can also be substituted by a R* substituent, and R* can be linked to the carrier either directly or via a linker group L. Of course, R* can also contain branching groups like e.g. tertiary amine and amide groups.

It is important for the purpose of the invention that the amine compound comprises at least one primary and/or secondary amine group to react with the perfume aldehyde and/or ketone to form the reaction products. Of course, the amine compound is not limited to having only one amine function. Indeed, more preferably, the amine compound comprises more than one amine function, thereby enabling the amine compound to react with several aldehydes and/or ketones. Accordingly, reaction products carrying mixed aldehyde(s) and/or ketone(s) can be achieved, thereby resulting in a mixed release of such fragrances.

Typical linker group include:

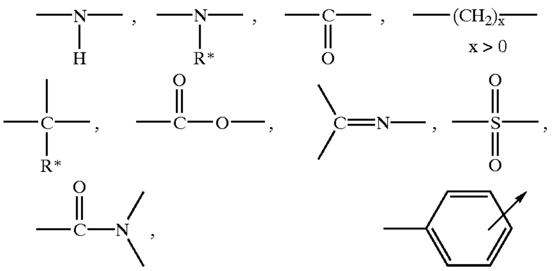

L can also be combination substitution in o, m, p-position e.g.

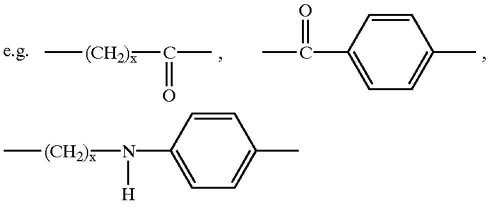

L can also contain —O— if this group is not directly linked to N e.g. $H_2N—CH_2—CH_2—O$ Most of the compounds described in the classes of amine compounds hereinafter will contain at least one substituent group classified as R*.

R* contains 1 to 22 carbon atoms in the main chain and optionally can be an alkyl, alkenyl, or alkylbenzene chain. It can also contain alicyclic, aromatic, heteroaromatic or heterocyclic systems, either inserted into the main chain or by substitution of an H atom of the main chain. Further, R* can either be linked to the carrier B material or via a linker L, as defined herein before. In this instance, L can also be —O—.

The main chain can contain from 1 to up to 15 R* groups.

Typical R* insertion groups include:

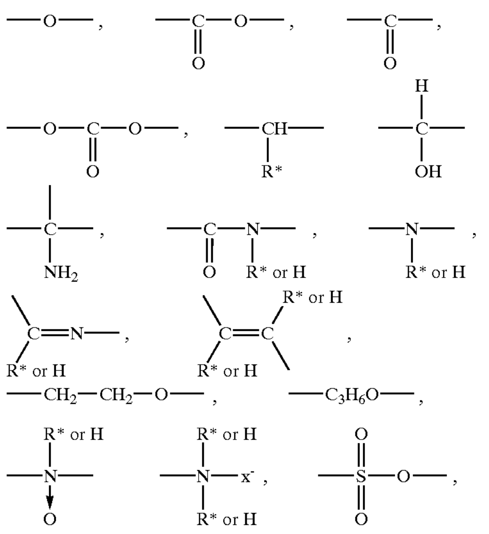

$x^-$ = anion

-continued

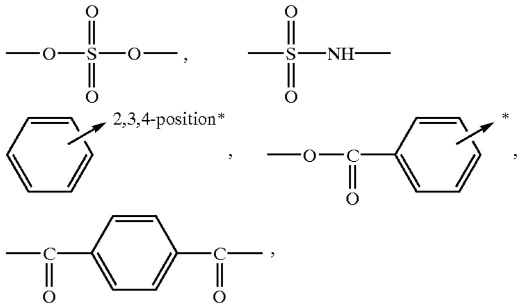

* the arrow indicates upto 3 substitutions in position 2,3,4

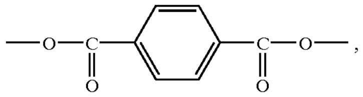

R* can also contain several insertion groups linked together: e.g.

e.g.:

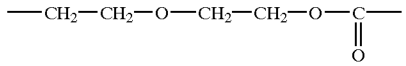

Furthermore, R* can carry a functional end group E that provides additional surface substantivity. Typical organic groups of this end group E include

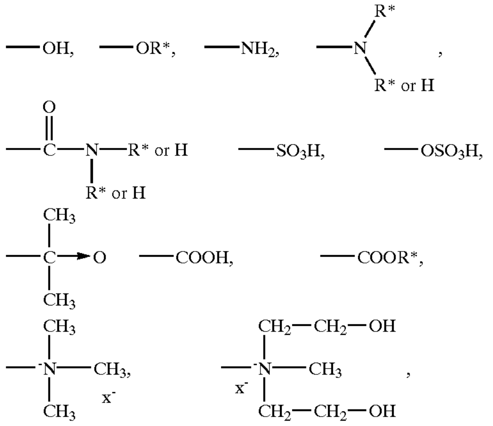

$x^-$= anion like $Cl^-$, $Br^-$, $SO_4^{2-}$, etc...

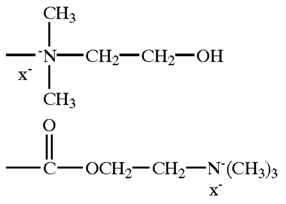

E can also be an aromatic, alicyclic, heteroaromatic, or heterocyclic group including mono-, di-, oligo-, polysaccharides

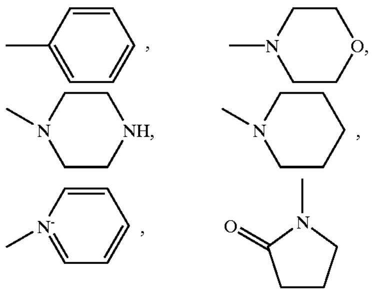

In addition, the R* group can also be modified via substitution of one or more H atoms in the main chain. The substitution group can either be E or the insertion groups as defined above where the insertion group is terminated by any of H, E, or R*.

R* can also be a group made of ethoxy or epoxy groups with n ranging from 1 to 15, including groups like:

$$—(CH_2CH_2O)_nH—(O—CH_2CH_2)_n—OH$$

$$—(C_3H_6O)_n—H—(O—C_3H_6)_n—OH$$

As defined herein before, preferred amine having organic carrier material B may be selected from aminoaryl derivatives, polyamines, aminoacids and derivatives, substituted amines and amides, glucamines, amino-substituted mono-, di-, oligo-, poly-saccharides, dendrimers and/or mixtures thereof.

1-Amino Aryl Derivatives

In this class of compounds, the amino group is preferably attached to a benzene ring. The benzene ring is further substituted in the para- and/or meta-position with R* as defined herein before. R* can be attached to the benzene ring via a linker L. The benzene ring can be substituted by other aromatic ring systems including naphtalene, indole, benzimidazole, pyrimidine, purine, and mixtures thereof.

Preferably, the R* is attached to the benzene ring in its para position.

Typical amino-benzene derivatives have the following formula:

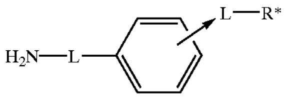

Preferred amino-benzene derivatives have the following formula:

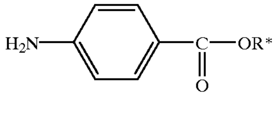

Preferred amino-benzene derivatives are alkyl esters of 4-amino benzoate compounds, preferably selected from ethyl-4-amino benzoate, phenylethyl-4-aminobenzoate, phenyl-4-aminobenzoate, 4-amino-N'-(3-aminopropyl)-benzamide, and mixtures thereof.

2-Polyamines

The polyamines of the invention need to have at least one, preferably more than one free and unmodified primary and/or secondary amine group, to react with the active aldehyde or ketone. In the polyamines, H can be substituted by R*, optionally via a linker group L. Additionally, the primary and/or secondary amine group can be linked to the polymer end via a linker group L.

The polyamines compounds suitable for use in the present invention are water-soluble or dispersible, polyamines. Typically, the polyamines for use herein have a molecular weight between 150 and $2*10^6$, preferably between 400 and $10^6$, most preferably between 5000 and $10^6$. These polyamines comprise backbones that can be either linear or cyclic. The polyamine backbones can also comprise polyamine branching chains to a greater or lesser degree. Preferably, the polyamine backbones described herein are modified in such a manner that at least one, preferably each nitrogen of the polyamine chain is thereafter described in terms of a unit that is substituted, quaternized, oxidized, or combinations thereof.

For the purposes of the present invention the term "modification" as it relates to the chemical structure of the polyamines is defined as replacing a backbone —NH hydrogen atom by an R' unit (substitution), quaternizing a backbone nitrogen (quaternized) or oxidizing a backbone nitrogen to the N-oxide (oxidized). The terms "modification" and "substitution" are used interchangeably when referring to the process of replacing a hydrogen atom attached to a backbone nitrogen with an R' unit. Quaternization or oxidation may take place in some circumstances without substitution, but substitution is preferably accompanied by oxidation or quatemization of at least one backbone nitrogen.

The linear or non-cyclic polyamine backbones that comprise the polyamine have the general formula:

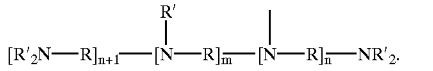

The cyclic polyamine backbones that comprise the polyamine have the general formula:

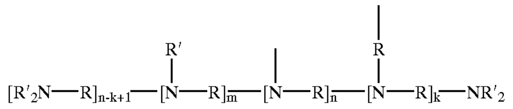

The above backbones prior to optional but preferred subsequent modification, comprise primary, secondary and tertiary amine nitrogens connected by R "linking" units.

For the purpose of the present invention, primary amine nitrogens comprising the backbone or branching chain once modified are defined as V or Z "terminal" units. For example, when a primary amine moiety, located at the end of the main polyamine backbone or branching chain having the structure

H2N—[R]— is modified according to the present invention, it is thereafter defined as a V "terminal" unit, or simply a V unit. However, for the purposes of the present invention, some or all of the primary amine moieties can remain unmodified subject to the restrictions further described herein below. These unmodified primary amine moieties by virtue of their position in the backbone chain remain "terminal" units. Likewise, when a primary amine moiety, located at the end of the main polyamine backbone having the structure

—NH2 is modified according to the present invention, it is thereafter defined as a Z "terminal" unit, or simply a Z unit. This unit can remain unmodified subject to the restrictions further described herein below.

In a similar manner, secondary amine nitrogens comprising the backbone or branching chain once modified are defined as W "backbone" units. For example, when a secondary amine moiety, the major constituent of the backbones and branching chains of the present invention, having the structure

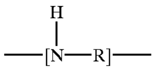

is modified according to the present invention, it is thereafter defined as a W "backbone" unit, or simply a W unit. However, for the purposes of the present invention, some or all of the secondary amine moieties can remain unmodified.

These unmodified secondary amine moieties by virtue of their position in the backbone chain remain "backbone" units.

In a further similar manner, tertiary amine nitrogens comprising the backbone or branching chain once modified are further referred to as Y "branching" units. For example, when a tertiary amine moiety, which is a chain branch point of either the polyamine backbone or other branching chains or rings, having the structure

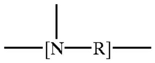

is modified according to the present invention, it is thereafter defined as a Y "branching" unit, or simply a Y unit. However, for the purposes of the present invention, some or all or the tertiary amine moieties can remain unmodified. These unmodified tertiary amine moieties by virtue of their position in the backbone chain remain "branching" units. The R units associated with the V, W and Y unit nitrogens which serve to connect the polyamine nitrogens, are described herein below.

The final modified structure of the polyamines of the present invention can be therefore represented by the general formula V(n+1)WmYnZ for linear polyamine and by the general formula V(n−k+1)WmYnY'kZ for cyclic polyamine. For the case of polyamines comprising rings, a Y' unit of the formula

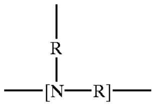

serves as a branch point for a backbone or branch ring. For every Y' unit there is a Y unit having the formula

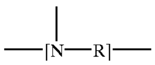

that will form the connection point of the ring to the main polymer chain or branch. In the unique case where the backbone is a complete ring, the polyamine backbone has the formula

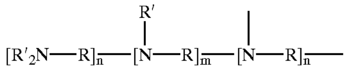

therefore comprising no Z terminal unit and having the formula

Vn-kWmYnY'k wherein k is the number of ring forming branching units. Preferably the polyamine backbones of the present invention comprise no rings.

In the case of non-cyclic polyamines, the ratio of the index n to the index m relates to the relative degree of branching. A fully non-branched linear modified polyamine according to the present invention has the formula VWmZ that is, n is equal to 0. The greater the value of n (the lower the ratio of m to n), the greater the degree of branching in the molecule. Typically the value for m ranges from a minimum value of 2 to 700, preferably 4 to 400, however larger values of m, especially when the value of the index n is very low or nearly 0, are also preferred.

Each polyamine nitrogen whether primary, secondary or tertiary, once modified according to the present invention, is further defined as being a member of one of three general classes; simple substituted, quaternized or oxidized. Those polyamine nitrogen units not modified are classed into V, W Y, Y' or Z units depending on whether they are primary, secondary or tertiary nitrogens. That is unmodified primary amine nitrogens are V or Z units, unmodified secondary amine nitrogens are W units or Y' units and unmodified tertiary amine nitrogens are Y units for the purposes of the present invention.

Modified primary amine moieties are defined as V "terminal" units having one of three forms:

a) simple substituted units having the structure:

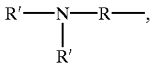

b) quaternized units having the structure:

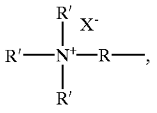

wherein X is a suitable counter ion providing charge balance; and c) oxidized units having the structure:

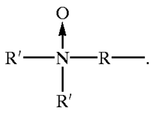

Modified secondary amine moieties are defined as W "backbone" units having one of three forms:

a) simple substituted units having the structure:

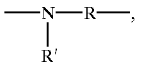

b) quaternized units having the structure:

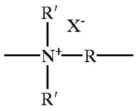

wherein X is a suitable counter ion providing charge balance; and c) oxidized units having the structure:

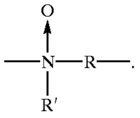

Other modified secondary amine moieties are defined as Y' units having one of three forms:

a) simple substituted units having the structure:

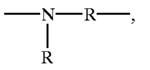

b) quaternized units having the structure:

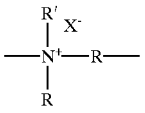

wherein X is a suitable counter ion providing charge balance; and c) oxidized units having the structure:

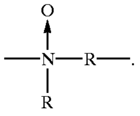

Modified tertiary amine moieties are defined as Y "branching" units having one of three forms:

a) unmodified units having the structure:

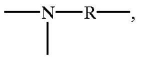

b) quaternized units having the structure:

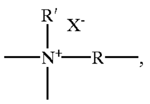

wherein X is a suitable counter ion providing charge balance; and c) oxidized units having the structure:

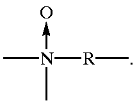

Certain modified primary amine moieties are defined as Z "terminal" units having one of three forms:

a) simple substituted units having the structure:

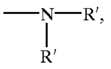

b) quaternized units having the structure:

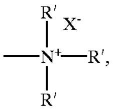

wherein X is a suitable counter ion providing charge balance; and c) oxidized units having the structure:

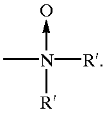

When any position on a nitrogen is unsubstituted of unmodified, it is understood that hydrogen will substitute for R'. For example, a primary amine unit comprising one R' unit in the form of a hydroxyethyl moiety is a V terminal unit having the formula (HOCH2CH2)HN—.

For the purposes of the present invention there are two types of chain terminating units, the V and Z units. The Z "terminal" unit derives from a terminal primary amino moiety of the structure —NH2. Non-cyclic polyamine backbones according to the present invention comprise only one Z unit whereas cyclic polyamines can comprise no Z units. The Z "terminal" unit can be substituted with any of the R' units described further herein below, except when the Z unit is modified to form an N-oxide. In the case where the Z unit nitrogen is oxidized to an N-oxide, the nitrogen must be modified and therefore R' cannot be a hydrogen.

The polyamines of the present invention comprise backbone R "linking" units that serve to connect the nitrogen atoms of the backbone. R units comprise units that for the purposes of the present invention are referred to as "hydrocarbyl R" units and "oxy R" units. The "hydrocarbyl" R units are C2–C12 alkylene, C4–C12 alkenylene, C3–C12 hydroxyalkylene wherein the hydroxyl moiety may take any position on the R unit chain except the carbon atoms directly connected to the polyamine backbone nitrogens; C4–C12 dihydroxyalkylene wherein the hydroxyl moieties may occupy any two of the carbon atoms of the R unit chain except those carbon atoms directly connected to the polyamine backbone nitrogens; C8–C12 dialkylarylene which for the purpose of the present invention are arylene moieties having two alkyl substituent groups as part of the linking chain. For example, a dialkylarylene unit has the formula

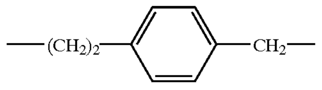

or

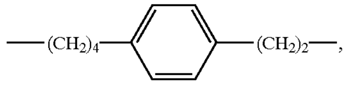

although the unit need not be 1,4-substituted, but can also be 1,2 or 1,3 substituted C2–C12 alkylene, preferably ethylene, 1,2-propylene, and mixtures thereof, more preferably ethylene. The "oxy" R units comprise —(R1O)xR5(OR1)x-, —CH2CH(OR2)CH2O)z(R1O)yR1(OCH2CH(OR2)CH2)w-, —CH2CH(OR2)CH2-, —(R1O)xR1-, and mixtures thereof. Preferred R units are selected from the group consisting of C2–C12 alkylene, C3–C12 hydroxyalkylene, C4–C12 dihydroxyalkylene, C8–C12 dialkylarylene, —(R1O)xR1-, —CH2CH(OR2)CH2-, —(CH2CH(OH)CH2O)z(R1O)yR1(OCH2CH—(OH)CH2)w-, —(R1O)xR5(OR1)x-, more preferred R units are C2–C12 alkylene, C3–C12 hydroxy-alkylene, C4–C12 dihydroxyalkylene, —(R1O)xR1-, —(R1O)xR5(OR1)x-, —(CH2CH(OH)CH2)z(R1 O)yR1(OCH2CH—(OH)CH2)w-, and mixtures thereof, even more preferred R units are C2–C12 alkylene, C3 hydroxyalkylene, and mixtures thereof, most preferred are C2–C6 alkylene. The most preferred backbones of the present invention comprise at least 50% R units that are ethylene.

R1 units are C2–C6 alkylene, and mixtures thereof, preferably ethylene. R2 is hydrogen, and —(R1O)xB, preferably hydrogen. R3 is C1–C18 alkyl, C7–C12 arylalkylene, C7–C12 alkyl substituted aryl, C6–C12 aryl, and mixtures thereof, preferably C1–C12 alkyl, C7–C12 arylalkylene, more preferably C1–C12 alkyl, most preferably methyl. R3 units serve as part of R' units described herein below.

R4 is C1–C12 alkylene, C4–C12 alkenylene, C8–C12 arylalkylene, C6–C10 arylene, preferably C1–C10 alkylene, C8–C12 arylalkylene, more preferably C2–C8 alkylene, most preferably ethylene or butylene.

R5 is C1–C12 alkylene, C3–C12 hydroxyalkylene, C4–C12 dihydroxyalkylene, C8–C12 dialkylarylene, —C(O)—, —C(O)NHR6NHC(O)—, —C(O)(R4)rC(O)—, —R1(OR1)-, —CH2CH(OH)CH2O(R1O)yR1OCH2CH(OH)CH2-, —C(O)(R4)rC(O)—, —CH2CH(OH)CH2-, R5 is preferably ethylene, —C(O)—, —C(O)NHR6NHC(O)—, —R1(OR1)-, —CH2CH(OH)CH2—, —CH2CH(OH)CH20(R1O)yR1OCH2CH—(OH)CH2-, more preferably —CH2CH(OH)CH2-. R6 is C2–C12 alkylene or C6–C12 arylene.

The preferred "oxy" R units are further defined in terms of the R1, R2, and R5 units. Preferred "oxy" R units comprise the preferred R1, R2, and R5 units. The preferred polyamines of the present invention comprise at least 50% RI units that are ethylene. Preferred R1, R2, and R5 units are combined with the "oxy" R units to yield the preferred "oxy" R units in the following manner.

i) Substituting more preferred R5 into —(CH2CH2O)xR5(OCH2CH2)x- yields —(CH2CH2O)xCH2CHOHCH2(OCH2CH2)x-.

ii) Substituting preferred R1 and R2 into —(CH2CH(OR2)CH2O)z-(R1O)yR1O(CH2CH(OR2)CH2)w- yields —(CH2CH(OH)CH2O)z-(CH2CH2O)yCH2CH2O(CH2CH(OH)CH2)w-.

iii) Substituting preferred R2 into —CH2CH(OR2)CH2- yields —CH2CH(OH)CH2-.

R' units are selected from the group consisting of hydrogen, C1–C22 alkyl, C3–C22 alkenyl, C7–C22 arylalkyl, C2–C22 hydroxyalkyl, —(CH2)pCO2M, —(CH2)qSO3M, —CH(CH2CO2M)CO2M, —(CH2)pPO3M, —(R1O)mB, —C(O)R3, preferably hydrogen, C2–C22 hydroxyalkylene, benzyl, C1–C22 alkylene, —(R1O)mB, —C(O)R3, —(CH2)pCO2M, —(CH2)qSO3M, —CH(CH2CO2M)CO2M, more preferably C1–C22 alkylene, —(R1O)xB, —C(O)R3, —(CH2)pCO2M, —(CH2)qSO3M, —CH(CH2CO2M)CO2M, most preferably C1–C22 alkylene, —(R1O)xB, and —C(O)R3. When no modification or substitution is made on a nitrogen then hydrogen atom will remain as the moiety representing R'. A most preferred R' unit is (R1O)xB. R' units do not comprise hydrogen atom when the V, W or Z units are oxidized, that is the nitrogens are N-oxides. For example, the backbone chain or branching chains do not comprise units of the following structure:

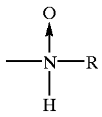 or 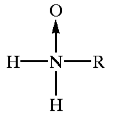 or 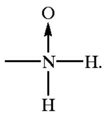

Additionally, R' units do not comprise carbonyl moieties directly bonded to a nitrogen atom when the V, W or Z units are oxidized, that is, the nitrogens are N-oxides. According to the present invention, the R' unit —C(O)R3 moiety is not bonded to an N-oxide modified nitrogen, that is, there are no N-oxide amides having the structure

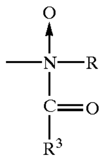 or 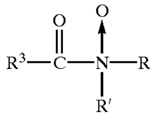 or 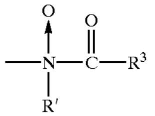

or combinations thereof.

B is hydrogen, C1–C6 alkyl, —(CH2)qSO3M, —(CH2)pCO2M, —(CH2)q- (CHSO3M)CH2SO3M, —(CH2)q(CHSO2M)CH2SO3M, —(CH2)pPO3M, —PO3M, preferably hydrogen, —(CH2)qSO3M, —(CH2)q(CHSO3M)CH2SO3M, —(CH2)q- (CHSO2M)CH2SO3M, more preferably hydrogen or —(CH2)qSO3M. M is hydrogen or a water soluble cation in sufficient amount to satisfy charge balance. For example, a sodium cation equally satisfies —(CH2)pCO2M, and —(CH2)qSO3M, thereby resulting in —(CH2)pCO2Na, and —(CH2)qSO3Na moieties. More than one monovalent cation, (sodium, potassium, etc.) can be combined to satisfy the required chemical charge balance. However, more than one anionic group may be charge balanced by a divalent cation, or more than one mono-valent cation may be necessary to satisfy the charge requirements of a poly-anionic radical. For example, a —(CH2)pPO3M moiety substituted with sodium atoms has the formula —(CH2)pPO3Na3. Divalent cations such as calcium (Ca2+) or magnesium (Mg2+) may be substituted for or combined with other suitable mono-valent water soluble cations. Preferred cations are sodium and potassium, more preferred is sodium.

X is a water soluble anion such as chlorine (Cl—), bromine (Br—) and iodine (I—) or X can be any negatively charged radical such as sulfate (SO42-) and methosulfate (CH3SO3-).

The formula indices have the following values: p has the value from 1 to 6, q has the value from 0 to 6; r has the value 0 or 1; w has the value 0 or 1, x has the value from 1 to 100;

y has the value from 0 to 100; z has the value 0 or 1; m has the value from 2 to 700, preferably from 4 to 400, n has the value from 0 to 350, preferably from 0 to 200; m+n has the value of at least 5. Preferably x has a value lying in the range of from 1 to 20, preferably from 1 to 10.

The preferred polyamines of the present invention comprise polyamine backbones wherein less than 50% of the R groups comprise "oxy" R units, preferably less than 20% , more preferably less than 5%, most preferably the R units comprise no "oxy" R units.

The most preferred polyamines which comprise no "oxy" R units comprise polyamine backbones wherein less than 50% of the R groups comprise more than 3 carbon atoms. For example, ethylene, 1,2-propylene, and 1,3-propylene comprise 3 or less carbon atoms and are the preferred "hydrocarbyl" R units. That is when backbone R units are C2–C12 alkylene, preferred is C2–C3 alkylene, most preferred is ethylene.

The polyamines of the present invention comprise modified homogeneous and non-homogeneous polyamine backbones, wherein 100% or less of the —NH units are modified. For the purpose of the present invention the term "homogeneous polyamine backbone" is defined as a polyamine backbone having R units that are the same (i.e., all ethylene). However, this sameness definition does not exclude polyamines that comprise other extraneous units comprising the polymer backbone which are present due to an artifact of the chosen method of chemical synthesis. For example, it is known to those skilled in the art that ethanolamine may be used as an "initiator" in the synthesis of polyethyleneimines, therefore a sample of polyethyleneimine that comprises one hydroxyethyl moiety resulting from the polymerization "initiator" would be considered to comprise a homogeneous polyamine backbone for the purposes of the present invention. A polyamine backbone comprising all ethylene R units wherein no branching Y units are present is a homogeneous backbone. A polyamine backbone comprising all ethylene R units is a homogeneous backbone regardless of the degree of branching or the number of cyclic branches present.

For the purposes of the present invention the term "non-homogeneous polymer backbone" refers to polyamine backbones that are a composite of various R unit lengths and R unit types. For example, a non-homogeneous backbone comprises R units that are a mixture of ethylene and 1,2-propylene units. For the purposes of the present invention a mixture of "hydrocarbyl" and "oxy" R units is not necessary to provide a non-homogeneous backbone.

Preferred polyamines of the present invention comprise homogeneous polyamine backbones that are totally or partially substituted by polyethyleneoxy moieties, totally or partially quaternized amines, nitrogens totally or partially oxidized to N-oxides, and mixtures thereof. However, not all backbone amine nitrogens must be modified in the same manner, the choice of modification being left to the specific needs of the formulator. The degree of ethoxylation is also determined by the specific requirements of the formulator.

The preferred polyamines that comprise the backbone of the compounds of the present invention are generally polyalkyleneimines (PAI's), preferably polyethyleneimines (PEI's), or PEI's connected by moieties having longer R units than the parent PAI's or PEI's.

Preferred amine polymer backbones comprise R units that are C2 alkylene (ethylene) units, also known as polyethylenimines (PEI's). Preferred PEI's have at least moderate branching, that is the ratio of m to n is less than 4:1, however PEI's having a ratio of m to n of 2:1 are most preferred.

Preferred backbones, prior to modification have the general formula:

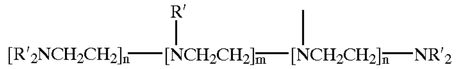

wherein R', m and n are the same as defined herein above. Preferred PEI's will have a molecular weight greater than 200 daltons.

The relative proportions of primary, secondary and tertiary amine units in the polyamine backbone, especially in the case of PEI's, will vary, depending on the manner of preparation. Each hydrogen atom attached to each nitrogen atom of the polyamine backbone chain represents a potential site for subsequent substitution, quaternization or oxidation.

These polyamines can be prepared, for example, by polymerizing ethyleneimine in the presence of a catalyst such as carbon dioxide, sodium bisulfite, sulfuric acid, hydrogen peroxide, hydrochloric acid, acetic acid, etc. Specific methods for preparing these polyamine backbones are disclosed in U.S. Pat. No. 2,182,306, Ulrich et al., issued Dec. 5, 1939; U.S. Pat. No. 3,033,746, Mayle et al., issued May 8, 1962; U.S. Pat. No. 2,208,095, Esselmann et al., issued Jul. 16, 1940; U.S. Pat. No. 2,806,839, Crowther, issued Sep. 17, 1957; and U.S. Pat. No. 2,553,696, Wilson, issued May 21, 1951; all herein incorporated by reference.

Still other polyamines suitable for use in the present invention are poly[oxy(methyl-1,2-ethanediyl)], α-(2-aminomethylethyl)-ω-(2-aminomethylethoxy)- (=C.A.S. No. 9046-10-0); poly[oxy(methyl-1,2-ethanediyl)], α-hydro-)-ω-(2-aminomethylethoxy)-, ether with 2-ethyl-2-(hydroxymethyl)-1,3-propanediol (=C.A.S. No. 39423-51-3); commercially available under the tradename Jeffamines T-403, D-230, D-400, D-2000; 2,2',2"-triaminotriethylamine; 2,2'-diamino-diethylamine; 3,3'-diamino-dipropyl-amine, 1,3 bis aminoethylcyclohexane commercially available from Mitsibushi and the C12 Sternamines commercially available from Clariant like the C12 Sternamin(propylenamine)$_n$ with n=¾, and mixtures thereof.

3-Amino Acids and Derivatives

Still other suitable compounds for use in the present invention are aminoacids and their derivatives, especially ester and amide derivatives. More preferred compounds are those providing enhanced surface substantivity due to its structural feature. For clarification, the term amino acids and derivatives does not encompass polymeric compounds.

Suitable amino acids have the following functionality of formula:

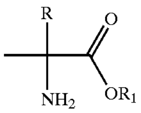

Wherein $R_1$=H, R* or (L)—R* and R is the amino acid side group, generally referred to as the "R group" such as in "Principles of Biochemistry" by Lehninger et al., 1997, Second Edition, Worth, pp114–116.

Preferred amino acids for use herein are selected tyrosine, tryptophane, lysine, glutamic acid, glutamine, aspartic acid, arginine, asparagine, phenylalanine, proline, glycine, serine, histidine, threonine, methionine, and mixture thereof, most preferably selected from tyrosine, tryptophane, and mixture thereof. Still other preferred compound are the amino acid derivatives selected from tyrosine ethylate, glycine methylate, tryptophane ethylate and mixture thereof, 4-Substituted Amines and Amides For clarification, the term substituted amines and amides does not encompass polymeric compounds. Substituted amine and amide compounds suitable for use herein have the following general formula:

NH2-L—R**, in which L is —CO— in case of an amide.

Other optional linker group may be as defined under R*.

R** is as defined herein before under R* with the proviso that it contains at least 6 carbon atoms and/or N atoms and/or cyclohexyl-, piperidine, piperazine, and other heterocyclic groups like:

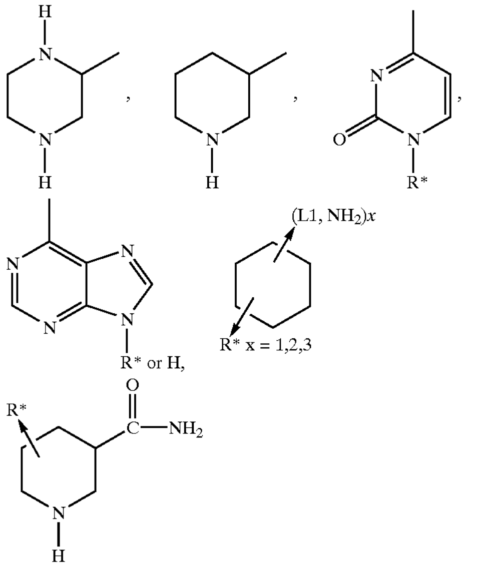

Optionally, H in NH can be substituted by R*.

Preferred polyamines are polyethyleneimines having the formula:

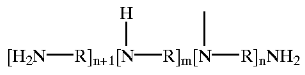

wherein the value of the indices n and m and the ratios thereof are such that they define the following polyamines commercially available under the tradename Lupasol like Lupasol FG which is characterized by the following: an average molecular weight of about 800 g/mol; a viscosity of 800 mPa at 20° C.; a pour point of about −3° C.; a density at 20° C. of about 1.09 g/mL; and a ratio of primary:secondary:tertiary amine nitrogens of about 1:0.82:0.53; Lupasol 20 wfr which is characterized by the following: an average molecular weight of about 1300 g/mol; a viscosity of about 5,000 mPa at 20° C.; a pour point of about −16° C.; a density at 20° C. of about 1.03 g/mL; and a ratio of primary:secondary:tertiary amine nitrogens of about 1:0.91:0.64; Lupasol PR 8515 which is characterized by the following: an average molecular weight of about 2000 g/mol; a viscosity of from about 300 mPa at 80° C. to about 75,000 mPa at 20° C.; a pour point of about −9° C.; a density at 20° C. of about 1.05 g/mL; and a ratio of primary:secondary:tertiary amine nitrogens of about 1:0.92:0.70; Lupasol WF which is characterized by the following: an average molecular weight of about 25,000 g/mol; a viscosity of from about 2500 mPa at 80° C. to about 200,000 mPa at 20° C.; a pour point of about −3° C.; a density at 20° of about 1.10 g/mL; a ratio of primary:secondary:tertiary arnine nitrogens of about 1:1.2:0.76; Lupasol FC which is characterized by the following: an average molecular weight of about 800 g/mol; a viscosity of about 250 mPa at 20° C.; a pour point of about −24° C.; a density at 20° C. of about 1.08 g/mL; and a ratio of primary:secondary:tertiary amine nitrogens of about 1:0.86:0.42; Lupasol G20 which is characterized by the following: an average molecular weight of about 1300 g/mol; a viscosity of about 350 mPa at 20° C.; a pour point of about −24° C.; a density at 20° C. of about 1.08 g/mL; and a ratio of primary:secondary:tertiary amine nitrogens of about 1:0.9:0.64; Lupasol G35 which is characterized by the following: an average molecular weight of about 2000 g/mol; a viscosity of about 450 mPa at 20° C.; a pour point of about −18° C.; a density at 20° C. of about 1.08 g/mL; and a ratio of primary:secondary:tertiary amine nitrogens of about 1:0.94:0.67; Lupasol G100 which is characterized by the following: an average molecular weight of about 5000 g/mol; a viscosity of about 1200 mPa at 20° C.; a pour point of about −18° C.; a density at 20° C. of about 1.08 g/mL; and a ratio of primary:secondary:tertiary amine nitrogens of about 1:1.05:0.76; Lupasol HF which is characterized by the following: an average molecular weight of about 25,000 g/mol; a viscosity of about 14,000 mPa at 20° C.; a pour point of about −20° C.; a density at 20° C. of about 1.08 g/mL; and a ratio of primary:secondary:tertiary amine nitrogens of about 1:1.2:0.76; Lupasol P which is characterized by the following: an average molecular weight of about 750,000 g/mol; a viscosity of from about 1000 mPa at 80° C. to about 500,000 mPa at 20° C.; a pour point of about −3° C. density at 20° C. of about 1.09 g/mL; and a ratio of primary:secondary:tertiary amine nitrogens of approximately 1:1.07:0.77; Lupasol PS which is characterized by the following: an average molecular weight of about 750, 000 g/mol; a viscosity of about 1400 mPa at 20° C.; a pour point of about −5° C.; and a ratio of primary:secondary:tertiary amine nitrogens of about 1:1.07:0.77; Lupasol SK which is characterized by the following: an average molecular weight of about 2,000,000 g/mol; a viscosity of about 750 mPa at 20° C.; a pour point of about 0° C.; and a density at 20° C. of about 1.06 g/mL; Lupasol SNA which is characterized by the following: an average molecular weight of about 1,000,000 g/mol; a viscosity of about 500 mPa at 20° C.; a pour point of about 0° C.; and a density at 20° C. of about 1.06 g/mL.

5-Glucamines

Still a further preferred class of amine compound is the class of glucamines of general structure:

NH2-CH2-(CH(OH))$_x$—CH2OH, wherein one or several OH-function can be substituted, preferably by —OR*, and wherein x is an integer of value 3 or 4. R* can be linked to the OH groups either directly or via linker unit as mentioned herein before under L.

For clarification, the term glucamine does not encompass polymeric compounds.

Preferred compound of this class are selected from 2,3, 4,5,6-pentamethoxy- glucamine; 6-acetylglucamine, glucamine, and mixture thereof.

6-Dendrimers

Another further class of amine compounds is the class of dendrimers. Suitable dendrimers carry free primary and/or secondary amine groups at the periphery of the spherical molecules, that can be reacted with (perfume) aldehydes or ketones to form the desired amine reaction product (perfume component) of the invention.

By dendrimers it is understood that the molecule is built up from a core molecule as described e.g. in WO 96/02588 and in Synthesis, February 1978, p. 155–158 or in Encyclopedia of Polymer Science & Engineering, 2nd ed., Hedstrand et al., in particular pages 46–91. The core is typically connected to multifunctional components to build up the "generations". For the purpose of the present invention, the nature of the inner generations is not critical. They can be based on e.g. polyamidoamines, polyamidoalcohols, polyethers, polyamides, polyethylenimines, etc. Important for the purpose of the present invention is that the outer generation(s) contain accessible primary and/or secondary amino functions.

Also suitable are the glyco dendrimers as described in e.g. Nachrichten aus Chemie 11 (1996), p. 1073–1079 and in WO 97/48711 provided that free primary and/or secondary amine groups are present at the surface of these molecules.

Preferred compounds are the polyethylenimine and polypropylenimine dendrimers, the commercially available Starburst® polyamidoamines (PAMAM) dendrimers, generation G0–G10 from Dendritech and the dendrimers Astromols®, generation 1–5 from DSM being DiAminoButane PolyAmine DAB (PA)x with $x=2^n \times 4$ and n being generally comprised between 0 and 4.

7-Amino-substituted Mono-, Di-, Oligo-, Poly-saccharides

Also suitable for the purpose of the present invention are specific amino-substituted mono-, di-, oligo-, poly-saccharides.

For the amino-substituted mono-saccharides of the present invention it is necessary that the hemi-acetal and/or hemi-ketal functionality is blocked via a suitable substituent to provide sufficient stability for the intended application. As indicated here above, glucoseamine is not a suitable amine. However, if the hemi-acetal OH function is substituted by R*, said monosaccharide becomes suitable for the purpose of the present invention. The amino group can be in position 2 to 5 or 6 depending on the type of monosaccharide and is preferably in C2, C5 or C6 position. Suitable amino-substituted mono-saccharides are:

C5 aldosen/ketosen: ribose, arabinose, xylose, lyxose, ribulose, xylulose;

C6 aldosen/ketosen: allose, altrose, glucose, mannose, gulose, idose, galactose, talose, fructose, sorbose, tagatose, psicose.

For amino-substituted di-saccharides with non-substituted aldose or ketose groups, the free OH-group needs to be substituted by R*, e.g. in lactose and maltose, whereas in sucrose there is no free acetal/ketal OH group. Optionally, more than one OH group can be substituted by R*. Suitable amino-substituted di-saccharides are amino substituted lactose, maltose, sucrose, cellobiose and trehalose.

Suitable amino-substituted oligo-, poly-saccharides are amino-substituted starch, cyclodextrin, dextran, glycogen, cellulose, mannan, gueran, levan, alternan glucose, mannose, galactose, fructose, lactose, maltose, sucrose, cellobiose, cyclodextrin, chitosan, and/or mixtures thereof. The molecules need to carry at least 1, preferably several, amino groups. Chitosan does not require additional amino substitution.

Also suitable for coupling carboxyl- or aldehyde-containing compounds are the following functionalised oligo-, poly-saccharides & glycans commercially available from the company Carbomer. Please find in brackets the reference number from Carbomer:

Amino alginate (5,00002), Diamino alginate (5,00003), Hexanediamine alginate (5,00004–5,00006–5,00008), dodecanediamine alginate (5,00005–5,00007–5,00009), 6-amino-6-deoxy cellulose (5,00020), O-ethylamine cellulose (5,00022), O-methylamine cellulose (5,00023), 3-amino-3-deoxy cellulose (5,00024), 2-amino-2 deoxy cellulose (5,00025), 2,3-diamino-2,3-dideoxy cellulose (5,00026), 6-[N-(1,6-hexanediamine)]-6-deoxy cellulose (5,00027), 6-[N-(1,12-docedanediamine)]-6-deoxy cellulose (5,00028), O-[methyl-(N-1,6-hexanediamine)] cellulose (5,00029), O-[methyl-(N-1,12-dodecanediamine)] cellulose (5,00030), 2,3-di-[N-(1,12-dodecanediamine)] cellulose (5,00031), 2,3-diamino-2,3-deoxy alpha-cyclodextrin (5,00050), 2,3-diamino-2,3-deoxy beta-cyclodextrin (5,00051), 2,3-diamino-2,3-deoxy gamma-cyclodextrin (5,00052), 6-amino-6-deoxy alpha-cyclodextrin (5,00053), 6-amino-6-deoxy beta-cyclodextrin (5,00054), O-ethyleamino beta-cyclodextrin (5,00055), 6[N-(1,6-hexanediamino)-6-deoxy alpha cyclodextrin (5,00056), 6[N-(1,6-hexanediamino)-6-deoxy beta cyclodextrin (5,00057), Amino dextran (5,00060), N-[di-(1,6-hexanediamine)] dextran (5,00061), N-[di-(1,12-dodecanediamine)] dextran (5,00062), 6-amino-6-deoxy-alpha-D-galactosyl-guaran (5,00070), O-ethylamino guaran (5,00071), Diamino guaran (5,00072), 6-amino-6-deoxy-starch (5,00080), O-ethylamino starch (5,00081), 2,3-diamine-2,3-dideoxy starch (5,00082), N-[6-(1,6-hexanediamine)]-6-deoxy starch (5,00083), N-[6-(1,12-dodecanediamine)]-6-deoxy starch (5,00084) and 2,3-di-[N (1,6-hexanediamine)]-2,3-dideoxy starch (5,00085)

Furthermore, with the use of some of the above compound comprising at least one primary and/or secondary amine group like the polyamine, the resulting amine reaction product will beneficially provide fabric appearance benefits, in particular color care and protection against fabric wear. Indeed, the appearance of fabrics, e.g., clothing, bedding, household fabrics like table linens is one of the area of concern to consumers. Indeed, upon typical consumer's uses of the fabrics such as wearing, washing, rinsing and/or tumble-drying of fabrics, a loss in the fabric appearance; which can be at least partly due to loss of color fidelity and color definition, is observed. Such a problem of color loss is even more acute after multiwash cycles. It has been found that the compositions of the present invention provide improved fabric appearance and protection against fabric wear and improved color care to laundered fabrics, especially after multiwash cycles.

Therefore, the compositions of the present invention can provide simultaneously fabric care and long lasting perfume benefits.

B-Active Ketone and/or Aldehyde

Preferably, for the above mentioned compounds, by active ketone or active aldehyde, it is meant any chain containing at least 1 carbon atom, preferably at least 5 carbon atoms.

Preferably, the active ketone or active aldehyde is respectively selected from a flavour ketone or aldehyde ingredient, a pharmaceutical ketone or aldehyde active, a biocontrol ketone or aldehyde agent, a perfume ketone or aldehyde component, a refreshing cooling ketone or aldehyde agent and mixtures thereof.

Flavour ingredients include spices, flavor enhancers that contribute to the overall flavour perception.

Pharmaceutical actives include drugs.

Biocontrol agents include biocides, antimicrobials, bactericides, fungicides, algaecides, mildewcides, disinfectants, antiseptics, insecticides, vermicides, plant growth hormones.

Biocontrol agents include biocides, antimicrobials, bactericides, fungicides, algaecides, mildewcides, disinfectants, sanitiser like bleach, antiseptics, insecticides, insect and/or moth repellant, vermicides, plant growth hormones.

Typical antimicrobials include Glutaraldehyde, Cinnamaldehyde, and mixtures thereof. Typical insect and/or moth repellants are perfume ingredients, such as citronelial, citral, N, N diethyl meta toluamide, Rotundial, 8-acetoxycarvotanacenone, and mixtures thereof. Other examples of insect and/or moth repellant for use herein are disclosed in U.S. Pat. Nos. 4,449,987, 4,693,890, 4,696,676, 4,933,371, 5,030,660, 5,196,200, and "Semio Activity of Flavor and Fragrance molecules on various Insect Species", B. D. Mookherjee et al., published in *Bioactive Volatile Compounds from Plants*, ASC Symposium Series 525, R. Teranishi, R. G. Buttery, and H. Sugisawa, 1993, pp. 35–48.

A typical disclosure of suitable ketone and/or aldehydes, traditionally used in perfumery, can be found in "perfume and Flavor Chemicals", Vol. I and II, S. Arctander, Allured Publishing, 1994, ISBN 0-931710-35-5.

Perfume ketones components include components having odoriferous properties.

Preferably, for the above mentioned compounds, the perfume ketone is selected for its odor character from buccoxime; iso jasmone; methyl beta naphthyl ketone; musk indanone; tonalid/musk plus; Alpha-Damascone, Beta-Damascone, Delta-Damascone, Iso-Damascone, Damascenone, Damarose, Methyl-Dihydrojasmonate, Menthone, Carvone, Camphor, Fenchone, Alpha-Ionone, Beta-Ionone, Gamma-Methyl so-called Ionone, Fleuramone, Dihydrojasmone, Cis-Jasmone, Iso-E-Super, Methyl-Cedrenyl-ketone or Methyl-Cedrylone, Acetophenone, Methyl-Acetophenone, Para-Methoxy-Acetophenone, Methyl-Beta-Naphtyl-Ketone, Benzyl-Acetone, Benzophenone, Para-Hydroxy-Phenyl-Butanone, Celery Ketone or Livescone, 6-Isopropyidecahydro-2-naphtone, Dimethyl-Octenone, Freskomenthe, 4-(1-Ethoxyvinyl)-3,3,5,5,-tetramethyl-Cyclohexanone, Methyl-Heptenone, 2-(2-(4-Methyl-3-cyclohexen-1-yl)propyl)-cyclopentanone, 1-(p-Menthen-6(2)-yl)-1-propanone, 4-(4-Hydroxy-3-methoxyphenyl)-2-butanone, 2-Acetyl-3,3-Dimethyl-Norbornane, 6,7-Dihydro-1,1,2,3,3-Pentamethyl-4(5H)-Indanone, 4-Damascol, Dulcinyl or Cassione, Gelsone, Hexalon, Isocyclemone E, Methyl Cyclocitrone, Methyl-Lavender-Ketone, Orivon, Para-tertiary-Butyl-Cyclohexanone, Verdone, Delphone, Muscone, Neobutenone, Plicatone, Veloutone, 2,4,4,7-Tetramethyl-oct-6-en-3-one, Tetrameran.

Preferably, for the above mentioned compounds, the preferred ketones are selected from Alpha Damascone, Delta Damascone, Iso Damascone, Carvone, Gamma-Methyl-Ionone, Iso-E-Super, 2,4,4,7-Tetramethyl-oct-6-en-3-one, Benzyl Acetone, Beta Damascone, Damascenone, methyl dihydrojasmonate, methyl cedrylone, and mixtures thereof.

Perfume aldehyde components include components having odoriferous properties.

Preferably, for the above mentioned compounds, the perfume aldehyde is selected for its odor character from adoxal; anisic aldehyde; cymal; ethyl vanillin; florhydral; helional; heliotropin; hydroxycitronellal; koavone; lauric aldehyde; lyral; methyl nonyl acetaldehyde; P. T. bucinal; phenyl acetaldehyde; undecylenic aldehyde; vanillin; 2,6, 10-trimethyl-9-undecenal, 3-dodecen-1-al, alpha-n-amyl cinnamic aldehyde, 4-methoxybenzaldehyde, benzaldehyde, 3-(4-tert butylphenyl)-propanal, 2-methyl-3-(para-methoxyphenyl propanal, 2-methyl-4-(2,6,6-trimethyl-2(1)-cyclohexen-1-yl)butanal, 3-phenyl-2-propenal, cis-/trans-3, 7-dimethyl-2,6-octadien-1-al, 3,7-dimethyl-6-octen-1-al, [(3,7-dimethyl-6-octenyl)oxy]acetaldehyde, 4-isopropylbenzyaldehyde, 1,2,3,4,5,6,7,8-octahydro-8,8-dimethyl-2-naphthaldehyde, 2,4-dimethyl-3-cyclohexen-1-carboxaldehyde, 2-methyl-3-(isopropylphenyl)propanal, 1-decanal; decyl aldehyde, 2,6-dimethyl-5-heptenal, 4-(tricyclo[5.2.1.0(2,6)]-decylidene-8)-butanal, octahydro-4,7-methano-1H-indenecarboxaldehyde, 3-ethoxy-4-hydroxy benzaldehyde, para-ethyl-alpha, alpha-dimethyl hydrocinnamaldehyde, alpha-methyl-3,4-(methylenedioxy)-hydrocinnamaldehyde, 3,4-methylenedioxybenzaldehyde, alpha-n-hexyl cinnamic aldehyde, m-cymene-7-carboxaldehyde, alpha-methyl phenyl acetaldehyde, 7-hydroxy-3,7-dimethyl octanal, Undecenal, 2,4,6-trimethyl-3-cyclohexene-1-carboxaldehyde, 4-(3)(4-methyl-3-pentenyl)-3-cyclohexen-carboxaldehyde, 1-dodecanal, 2,4-dimethyl cyclohexene-3-carbox-aldehyde, 4-(4-hydroxy-4-methyl pentyl)-3-cylohexene-1-carboxaldehyde, 7-methoxy-3,7-dimethyloctan-1-al, 2-methyl undecanal, 2-methyl decanal, 1-nonanal, 1-octanal, 2,6,10-trimethyl-5,9-undecadienal, 2 -methyl-3-(4-tertbutyl)propanal, dihydrocinnamic aldehyde, 1-methyl-4-(4-methyl-3-pentenyl)-3-cyclo-hexene-1-carboxaldehyde, 5 or 6 methoxyohexahydro-4,7-methanoindan-1 or 2-carboxaldehyde, 3,7-dimethyloctan-1-al, 1-undecanal, 10-undecen-1-al, 4-hydroxy-3-methoxy benzaldehyde, 1-methyl-3-(4-methylpentyl)-3-cyclhexene-carboxaldehyde, 7-hydroxy-3,7-dimethyl-octanal, trans4-decenal, 2,6-nonadienal, para-tolylacetaldehyde; 4-methylphenylacetaldehyde, 2-methyl-4-(2,6,6-trimethyl-1-cyclohexen-1-yl)-2-butenal, ortho-methoxycinnamic aldehyde, 3,5,6-trimethyl-3-cyclohexene carboxaldehyde, 3,7-dimethyl-2-methylene-6-octenal, phenoxyacetaldehyde, 5,9-dimethyl-4,8-decadienal, peony aldehyde (6,10-dimethyl-3-oxa-5,9-undecadien-1-al), hexahydro4,7-methanoindan-1-carboxaldehyde, 2-methyl octanal, alpha-methyl-4-(1-methyl ethyl) benzene acetaldehyde, 6,6-dimethyl-2-norpinene-2-propionaldehyde, para methyl phenoxy acetaldehyde, 2-methyl-3-phenyl-2-propen-1-al, 3,5,5-trimethyl hexanal, Hexahydro-8,8-dimethyl-2-naphthaldehyde, 3-propyl-bicyclo[2.2.1]hept-5-ene-2-carbaldehyde, 9-decenal, 3-methyl-5-phenyl-1-pentanal, methylnonyl acetaldehyde, hexanal, trans-2-hexenal, 1-p-menthene-q-carboxaldehyde and mixtures thereof.

Most preferred aldehydes are selected from 1-decanal, benzaldehyde, florhydral, 2,4-dimethyl-3-cyclohexen-1-carboxaldehyde; cis/trans-3,7-dimethyl-2,6-octadien-1-al; heliotropin; 2,4,6-trimethyl-3-cyclohexene-1-carboxaldehyde; 2,6-nonadienal; alpha-n-amyl cinnamic aldehyde, alpha-n-hexyl cinnamic aldehyde, P.T. Bucinal, lyral, cymal, methyl nonyl acetaldehyde, hexanal, trans-2-hexenal, and mixture thereof.

In the above list of perfume ingredients, some are commercial names conventionally known to one skilled in the art, and also includes isomers. Such isomers are also suitable for use in the present invention.

In another embodiment, especially suitable for the purpose of the present invention are the perfume compounds, preferably the perfume ketones or active aldehydes, characterised by having a low Odor Detection Threshold. Such Odor Detection Threshold (ODT) should be lower than or equal to 1 ppm, preferably lower than or equal to 10 ppb—measured at controlled Gas Chromatography (GC) conditions such as described here below. This parameter refers to the value commonly used in the perfumery arts and which is the lowest concentration at which significant detection takes place that some odorous material is present. Please refer for example in "Compilation of Odor and Taste Threshold Value Data (ASTM DS 48 A)", edited by F. A. Fazzalari, International Business Machines, Hopwell Junction, N.Y. and in Calkin et al., Perfumery, Practice and Principles, John Willey & Sons, Inc., page 243 et seq (1994). For the purpose of the present invention, the Odor Detection Threshold is measured according to the following method: The gas chromatograph is characterized to determine the exact volume of material injected by the syringe, the precise split ratio, and the hydrocarbon response using a hydrocarbon standard of known concentration and chain-length distribution. The air flow rate is accurately measured and, assuming the duration of a human inhalation to last 0.02 minutes, the sampled volume is calculated. Since the precise concentration at the detector at any point in time is known, the mass per volume inhaled is known and hence the concentration of material. To determine the ODT of a perfume material, solutions are delivered to the sniff port at the back-calculated concentration. A panelist sniffs the GC effluent and identifies the retention time when odor is noticed. The average over all panelists determines the threshold of noticeability. The necessary amount of analyte is injected onto the column to achieve a certain concentration, such as 10 ppb, at the detector. Typical gas chromatograph parameters for determining odor detection thresholds are listed below.

GC: 5890 Series II with FID detector

7673 Autosampler

Column: J & W Scientific DB-1

Length 30 meters ID 0.25 mm film thickness 1 micron

Method:

Split Injection: 17/1 split ratio

Autosampler: 1.13 microliters per injection

Column Flow: 1.10 mL/minute

Air Flow: 345 muminute

Inlet Temp. 245° C.

Detector Temp. 285° C.

Temperature Information

Initial Temperature: 50° C.

Rate: 5 C./minute

Final Temperature: 280° C.

Final Time: 6 minutes

Leading assumptions: 0.02 minutes per sniff

GC air adds to sample dilution

Examples of such preferred perfume components are those selected from: 2-methyl-2-(para-iso-propylphenyl)-propionaldehyde, 1-(2,6,6-trimethyl-2-cyclohexan-1-yl)-2-buten-1-one and/or para-methoxy-acetophenone. Even more preferred are the following compounds having an ODT≦10 ppb measured with the method described above: undecylenic aldehyde, undecalactone gamma, heliotropin, dodecalactone gamma, p-anisic aldehyde, para hydroxy-phenyl-butanone, cymal, benzyl acetone, ionone alpha, p.t.bucinal, damascenone, ionone beta and methyl-nonyl ketone.

Typically the level of active is of from 10 to 90%, preferably from 30 to 85%, more preferably from 45 to 80% by weight of the amine reaction product.

Preferred amine reaction products are those resulting from the reaction of polethyleneimine polymer like Lupasol polymers, with one or more of the following Alpha Damascone, Delta Damascone, Carvone, Hedione, Florhydral, Lilial, Heliotropine, Gamma-Methyl-Ionone and 2,4-dimethyl-3-cyclohexen-1-carboxaldehyde. Still other preferred amine reaction products are those resulting from the reaction of Astramol Dendrimers with Carvone as well as those resulting from the reaction of ethyl-4-amino benzoate with 2,4-dimethyl-3-cyclohexen-1-carboxaldehyde.

Most preferred amine reaction products are those from the reaction of Lupasol HF with Delta Damascone; LupasolG35 with -Alpha Damascone; LupasolG100 with 2,4-dimethyl-3-cyclohexen-1-carboxaldehyde, ethyl-4-amino benzoate with 2,4-dimethyl-3-cyclohexen-1-carboxaldehyde.

Process

Preparation of the component is made as follows in the Synthesis Examples. In general, the nitrogen analogs of ketones and aldehydes are called azomethines, Schiff bases or the more preferred name imines. These imines can easily be prepared by condensation of primary amines and carbonyl compounds by elimination of water.

A typical reaction profile is as follows:

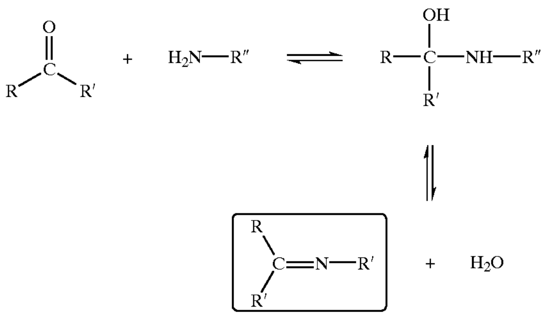

α,β-Unsaturated ketones do not only condense with amines to form imines, but can also undergo a competitive 1,4-addition to form β-aminoketones.

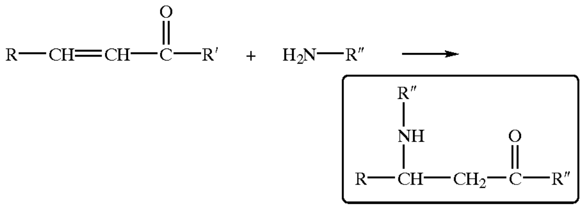

By means of this simple method, compound and composition containing said compounds are made which achieve a delayed release of the active ingredient.

As can be observed, the perfume ingredient is typically present in equimolar amount to the amine function so as to enable the reaction to take place and provide the resulting amine reaction product. Of course, higher amount are not excluded and even preferred when the amine compound comprises more than one amine function. When the amine compound has more than one free primary and/or secondary amine function, several different perfume raw materials can be linked to the amine compound.

Mechanism of Release

By the present invention, a delayed release of a perfume ingredient, i.e. ketone or aldehyde is obtained. Not to be bound by theory, the release is believed to occur by the following mechanisms:

For imine compounds, the perfume components are released upon breaking down of the imine bond, leading to the release of the perfume component and of the primary amine compound. This can be achieved by either hydrolysis, photochemical cleavage, oxidative cleavage, or enzymatic cleavage.

For β-aminoketone compounds, treatment with air moisture and/or water successfully releases the perfume component and the amine compound. However, other means of release are not excluded like hydrolysis, photochemical cleavage, oxidative cleavage, or enzymatic cleavage.

Still other means of release for imine as well as β-aminoketone compounds can be considered such as by the steaming step of ironing the treated fabric, tumble-drying, and/or wearing.

Applications Compositions

The present invention application compositions include compositions where there is a need of a delayed release of an active ketone or aldehyde. This includes compositions for use in the rinse such as softening compositions, personal cleansing such as shower gels, deodorants, bars, shampoos; stand alone compositions such deodorising compositions, insecticides, etc . . . Preferred are those compositions which result in contacting the compound of the invention with fabric. The composition of the invention are suitable for use in any step of the domestic treatment, that is a pre- and/or post-treatment composition, as a wash additive, as a composition suitable for use in the rinse process. Obviously, multiple applications can be made such as treating the fabric with a pre-treatment composition of the invention and thereafter with the composition suitable for use in the rinse process and/or drying process.

By compositions suitable for use in the rinse process, these are to be understood to include compositions such as rinse added fabric softener compositions and dryer added compositions (e.g. sheets) which provide softening and/or antistatic benefits, as well as rinse additives.

Preferred are those compositions which result in contacting the compound of the invention with fabric. These are to be understood to include compositions such as rinse added fabric softener compositions and dryer added compositions (e.g. sheets) which provide softening and/or antistatic benefits.

Preferably, the amine reaction product(s) which is incorporated into such compositions provides a dry surface Odor Index of more than 5 preferably at least 10.

By Dry Surface Odor Index, it is meant that the amine reaction product(s) provides a Delta of more than 5, wherein Delta is the difference between the Odor Index of the dry surface treated with amine reaction product(s) and of the Odor Index of the dry surface treated with only the perfume raw material.

Measurement Method of Dry Surface Odor Index for Fabric Surface

Product Preparation

The amine reaction product is added to the unperfumed product base.

The unperfumed product base, wherein the abreviations are as defined herein after for the examples, is as follows:

| Component | % by weight |
|---|---|
| DEQA | 19.0 |
| HCl | 0.02 |
| PEG | 0.6 |
| Silicone antifoam | 0.01 |
| Electrolyte (ppm) | 1200 |
| Dye (ppm) | 50 |
| Water and minors to balance to 100% | |

Levels of amine reaction product are selected so as to obtain an odor grade on the dry fabric of at least 20. After careful mixing, by shaking the container in case of a liquid, with a spatula in case of a powder, the product is allowed to sit for 24 hrs.

Washing Process

The resulting product is added into the washing machine in the dosage and in the dispenser appropriate for its category. The quantity corresponds to recommended dosages made for the corresponding market products: typically between 70 and 150 g for a detergent powder or liquid via current dosing device like granulette, or ariellette, and 25 and 40 ml for a liquid fabric softener. The load is composed of four bath towels (170 g) using a Miele W830 washing machine at 40° C. short cycle, water input: 15°Hardness at a temperature of 10–18° C., and full spin of 1200 rpm.

The same process is applied for the corresponding free perfume ingredient in consideration and is used as the reference. Dosages, fabric loads and washing cycles for the reference and the sample are identical.

Drying Process

Within two hours after the end of the washing cycle, the spinned but still wet fabrics are assessed for their odors using the scale mentioned below. Afterwards, half of the fabric pieces are hung on a line for 24 hr drying, away from any possible contaminations. Unless specified, this drying takes place indoor. Ambient conditions are at temperature between 18–25 C. and air moisture between 50–80%. The other half is placed in a tumble drier and undergoes a full "very dry" cycle, i.e. in a Miele, Novotronic T430 set on program white-extra dry (full cycle). Tumble dry fabrics are also assessed on the next day. Fabrics are then stored in opened aluminum bags in an odor free room, and assessed again after 7 days.

Odor Evaluations

Odor is assessed by expert panellists smelling carefully the fabrics. A 0–100 scale is used for all fabric odor gradings. The grading scale is as follows:

100=extremely strong perfume odor

75=very strong perfume odor

50=strong odor

40=moderate perfume odor

30=slight perfume odor

20=weak perfume odor

10=very weak perfume odor

0=no odor

A difference of more than 5 grades after 1 day and/or 7 days between the amine reaction product and the perfume raw material is statistically significant. A difference of 10 grades or more after one day and/or 7 days represents a step-change. In other words, when a difference of grade of more than 5, preferably at least 10 is observed between the amine reaction product and the perfume raw material, after either 1 day or 7 day or both 1 day and 7 days, it can be concluded that the amine reaction product is suitable for use in the present invention, provided that the amine compound fulfill the Odor Intensity Index.

The amine reaction product as defined herein before typically is comprised at from 0.0001% to 10%, preferably from 0.001% to 5%, and more preferably from 0.01% to 2%, by weight of the composition. Mixtures of the compounds may also be used herein.

Incorporation of the amine reaction product in the invention compositions can conveniently, if necessary, be carried out by conventional incorporation means, such as by spray-on, encapsulation like starch encapsulation, e.g. such as described in GB1464616, dry addition, or by encapsulation in cyclodextrin. Preferably, the amine reaction product is preformed before incorporation into the invention compositions. In other words, the perfume component and the amine compound are first reacted together to obtain the resulting amine reaction product as defined in the present invention and only once formed incorporated into the invention compositions. By being preformed before the incorporation in fully formulated composition, a better control of the compound being made is obtained. Hence, the interaction with perfume composition which may be present in fully formulated composition is avoided as well as side reaction that could occur. Further, by such means of incorporation, efficient control of the yield and purity of the compound is obtained.

Most preferably, when the invention composition comprises a perfume, the amine reaction product is incorporated in the composition separately from the perfume. By this means, the amine reaction product and its subsequent perfume release is more controlled.

Typically the invention composition comprises surfactancy ingredients such as a fabric softening agent, or a surfactant as described hereinafter as optional ingredients.

When the compositions comprises a softening agent, the resulting composition is a softening composition.

Fabric Softening Agents

A fabric softener component provides softness and antistastic properties to the treated fabrics. When used, the fabric softener component will typically be present at a level sufficient to provide softening and antistatic properties.

Said fabric softening component may be selected from cationic, nonionic, amphoteric or anionic fabric softening component.

Typical of the cationic softening components are the quaternary ammonium compounds or amine precursors thereof as defined hereinafter.

A)-Quaternary Ammonium Fabric Softening Active Compound (1) Preferred quaternary ammonium fabric softening active compound have the formula (1)

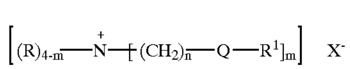

or the formula:

(2)

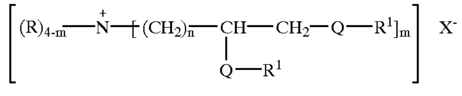

wherein Q is a carbonyl unit having the formula:

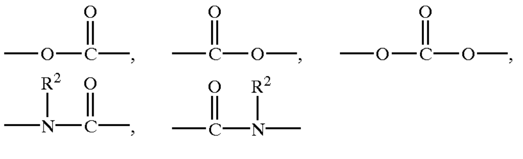

each R unit is independently hydrogen, $C_1$–$C_6$ alkyl, $C_1$–$C_6$ hydroxyalkyl, and mixtures thereof, preferably methyl or hydroxy alkyl; each $R^1$ unit is independently linear or branched $C_{11}$–$C_{22}$ alkyl, linear or branched $C_{11}$–$C_{22}$ alkenyl, and mixtures thereof, $R^2$ is hydrogen, $C_1$–$C_4$ alkyl, $C_1$–$C_4$ hydroxyalkyl, and mixtures thereof; X is an anion which is compatible with fabric softener actives and adjunct ingredients; the index m is from 1 to 4, preferably 2; the index n is from 1 to 4, preferably 2.

An example of a preferred fabric softener active is a mixture of quaternized amines having the formula:

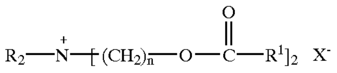

wherein R is preferably methyl; $R^1$ is a linear or branched alkyl or alkenyl chain comprising at least 11 atoms, preferably at least 15 atoms. In the above fabric softener example, the unit —$O_2CR^1$ represents a fatty acyl unit which is typically derived from a triglyceride source. The triglyceride source is preferably derived from tallow, partially hydrogenated tallow, lard, partially hydrogenated lard, vegetable oils and/or partially hydrogenated vegetable oils, such as, canola oil, safflower oil, peanut oil, sunflower oil, corn oil, soybean oil, tall oil, rice bran oil, etc. and mixtures of these oils.

The preferred fabric softening actives of the present invention are the Diester and/or Diamide Quaternary Ammonium (DEQA) compounds, the diesters and diamides having the formula:

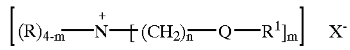

wherein R, $R^1$, X, and n are the same as defined herein above for formulae (1) and (2), and Q has the formula:

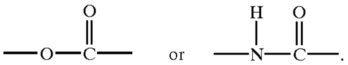

These preferred fabric softening actives are formed from the reaction of an amine with a fatty acyl unit to form an amine intermediate having the formula:

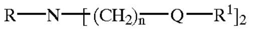

wherein R is preferably methyl, Q and $R^1$ are as defined herein before; followed by quaternization to the final softener active.

Non-limiting examples of preferred amines which are used to form the DEQA fabric softening actives according to the present invention include methyl bis(2-hydroxyethyl) amine having the formula:

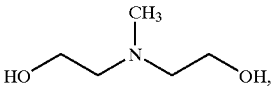

methyl bis(2-hydroxypropyl)amine having the formula:

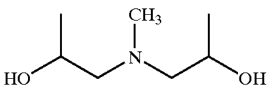

methyl(3-aminopropyl)(2-hydroxyethyl)amine having the formula:

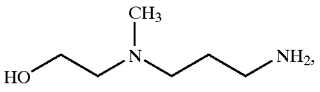

methyl bis(2-aminoethyl)amine having the formula:

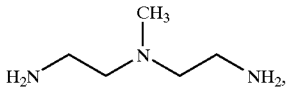

triethanol amine having the formula:

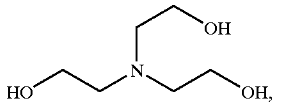

di(2-aminoethyl)ethanolamine having the formula:

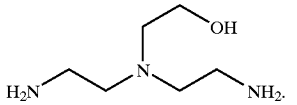

The counterion, $X^{(-)}$ above, can be any softener-compatible anion, preferably the anion of a strong acid, for example, chloride, bromide, methylsulfate, ethylsulfate, sulfate, nitrate and the like, more preferably chloride or methyl sulfate. The anion can also, but less preferably, carry a double charge in which case $X^{(-)}$ represents half a group.

Tallow and canola oil are convenient and inexpensive sources of fatty acyl units which are suitable for use in the present invention as $R^1$ units. The following are non-limiting examples of quaternary ammonium compounds suitable for use in the compositions of the present invention. The term "tallowyl" as used herein below indicates the $R^1$ unit is derived from a tallow triglyceride source and is a mixture of fatty acyl units. Likewise, the use of the term canolyl refers to a mixture of fatty acyl units derived from canola oil.

TABLE II

| Fabric Softener Actives |
|---|
| N,N-di(tallowyl-oxy-ethyl)-N,N-dimethyl ammonium chloride; |
| N,N-di(canolyl-oxy-ethyl)-N,N-dimethyl ammonium chloride; |
| N,N-di(tallowyl-oxy-ethyl)-N-methyl, N-(2-hydroxyethyl) ammonium chloride; |
| N,N-di(canolyl-oxy-ethyl)-N-methyl, N-(2-hydroxyethyl) ammonium chloride; |
| N,N-di(2-tallowyloxy-2-oxo-ethyl)-N,N-dimethyl ammonium chloride; |
| N,N-di(2-canolyloxy-2-oxo-ethyl)-N,N-dimethyl ammonium chloride |
| N,N-di(2-tallowyloxyethylcarbonyloxyethyl)-N,N-dimethyl ammonium chloride; |
| N,N-di(2-canolyloxyethylcarbonyloxyethyl)-N,N-dimethyl ammonium chloride; |
| N-(2-tallowoyloxy-2-ethyl)-N-(2-tallowyloxy-2-oxo-ethyl)-N,N-dimethyl ammonium chloride; |
| N-(2-canolyloxy-2-ethyl)-N-(2-canolyloxy-2-oxo-ethyl)-N,N-dimethyl ammonium chloride; |
| N,N,N-tri(tallowyl-oxy-ethyl)-N-methyl ammonium chloride; |
| N,N,N-tricanolyl-oxy-ethyl)-N-methyl ammonium chloride; |
| N-(2-tallowyloxy-2-oxoethyl)-N-(tallowyl)-N,N-dimethyl ammonium chloride; |
| N-(2-canolyloxy-2-oxoethyl)-N-(canolyl)-N,N-dimethyl ammonium chloride; |
| 1,2-ditallowyloxy-3-N,N,N-trimethylammoniopropane chloride; and |
| 1,2-dicanolyloxy-3-N,N,N-trimethylammoniopropane chloride, |
| and mixtures of the above actives. |

Other examples of quaternay ammoniun softening compounds are methylbis(tallowamidoethyl)(2-hydroxyethyl) ammonium methylsulfate and methylbis(hydrogenated tallowamidoethyl)(2-hydroxyethyl)ammonium methylsulfate; these materials are available from Witco Chemical Company under the trade names Varisoft® 222 and Varisoft® 110, respectively.

Particularly preferred is N,N-di(tallowoyl-oxy-ethyl)-N,N-dimethyl ammonium chloride, where the tallow chains are at least partially unsaturated.

The level of unsaturation contained within the tallow, canola, or other fatty acyl unit chain can be measured by the Iodine Value (IV) of the corresponding fatty acid, which in the present case should preferably be in the range of from 5 to 100 with two categories of compounds being distinguished, having a IV below or above 25.

Indeed, for compounds having the formula:

$$\left[(R)_{4-m}-\overset{+}{N}-\left[(CH_2)_n-Q-R^1\right]_m\right] \quad X^-$$

derived from tallow fatty acids, when the Iodine Value is from 5 to 25, preferably 15 to 20, it has been found that a cis/trans isomer weight ratio greater than 30/70, preferably greater than 50/50 and more preferably greater than 70/30 provides optimal concentrability.

For compounds of this type made from tallow fatty acids having a Iodine Value of above 25, the ratio of cis to trans isomers has been found to be less critical unless very high concentrations are needed.

Other suitable examples of fabric softener actives are derived from fatty acyl groups wherein the terms "tallowyl" and canolyl" in the above examples are replaced by the terms "cocoyl, palmyl, lauryl, oleyl, ricinoleyl, stearyl, palmityl," which correspond to the triglyceride source from which the fatty acyl units are derived. These alternative fatty acyl sources can comprise either fully saturated, or preferably at least partly unsaturated chains.

As described herein before, R units are preferably methyl, however, suitable fabric softener actives are described by replacing the term "methyl" in the above examples in Table II with the units "ethyl, ethoxy, propyl, propoxy, isopropyl, butyl, isobutyl and t-butyl.

The counter ion, X, in the examples of Table II can be suitably replaced by bromide, methylsulfate, formate, sulfate, nitrate, and mixtures thereof. In fact, the anion, X, is merely present as a counterion of the positively charged quaternary ammonium compounds. The scope of this invention is not considered limited to any particular anion.

For the preceding ester fabric softening agents, the pH of the compositions herein is an important parameter of the present invention. Indeed, it influences the stability of the quaternary ammonium or amine precursors compounds, especially in prolonged storage conditions.

The pH, as defined in the present context, is measured in the neat compositions at 20° C. While these compositions are operable at pH of less than 6.0, for optimum hydrolytic stability of these compositions, the neat pH, measured in the above-mentioned conditions, must preferably be in the range of from 2.0 to 5, preferably in the range of 2.5 to 4.5, preferably 2.5 to 3.5. The pH of these compositions herein can be regulated by the addition of a Bronsted acid.

Examples of suitable acids include the inorganic mineral acids, carboxylic acids, in particular the low molecular weight ($C_1$–$C_5$) carboxylic acids, and alkylsulfonic acids. Suitable inorganic acids include HCl, $H_2SO_4$, $HNO_3$ and $H_3PO_4$. Suitable organic acids include formic, acetic, citric, methylsulfonic and ethylsulfonic acid. Preferred acids are citric, hydrochloric, phosphoric, formic, methylsulfonic acid, and benzoic acids.

As used herein, when the diester is specified, it will include the monoester that is normally present in manufacture. For softening, under no/low detergent carry-over laundry conditions the percentage of monoester should be as low as possible, preferably no more than 2.5%. However, under high detergent carry-over conditions, some monoester is preferred. The overall ratios of diester to monoester are from 100:1 to 2:1, preferably from 50:1 to 5:1, more preferably from 13:1 to 8:1. Under high detergent carry-over conditions, the di/monoester ratio is preferably 11:1. The level of monoester present can be controlled in the manufacturing of the softener compound.

Mixtures of actives of formula (1) and (2) may also be prepared.

2)-Still other suitable quaternary ammonium fabric softening compounds for use herein are cationic nitrogenous salts having two or more long -chain acyclic aliphatic $C_8$–$C_{22}$ hydrocarbon groups or one said group and an arylalkyl group which can be used either alone or as part of a mixture are selected from the group consisting of:

(i) acyclic quaternary ammonium salts having the formula:

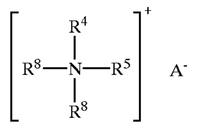

wherein $R^4$ is an acyclic aliphatic $C_8$–$C_{22}$ hydrocarbon group, $R^5$ is a $C_1$–$C_4$ saturated alkyl or hydroxyalkyl group, $R^8$ is selected from the group consisting of $R^4$ and $R^5$ groups, and A– is an anion defined as above;

(ii) diamino alkoxylated quaternary ammonium salts having the formula:

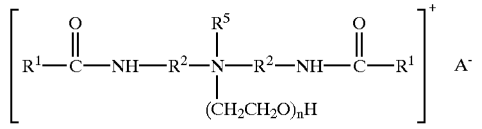

wherein n is equal to 1 to 5, and $R^1$, $R^2$, $R^5$ and $A^-$ are as defined above;

(iii) mixtures thereof.

Examples of the above class cationic nitrogenous salts are the well-known dialkyldi methylammonium salts such as ditallowdimethylammonium chloride, ditallowdimethylammonium methylsulfate, di(hydrogenatedtallow) dimethylammonium chloride, distearyidimethylammonium chloride, dibehenyidimethylammonium chloride. Di(hydrogenatedtallow)di methylammonium chloride and ditallowdimethylammonium chloride are preferred. Examples of commercially available dialkyldimethyl ammonium salts usable in the present invention are di(hydrogenatedtallow)dimethylammonium chloride (trade name Adogen® 442), ditallowdimethylammonium chloride (trade name Adogen® 470, Praepagen® 3445), distearyl dimethylammonium chloride (trade name Arosurf® TA-100), all available from Witco Chemical Company. Dibehenyidimethylammonium chloride is sold under the trade name Kemamine Q-2802C by Humko Chemical Division of Witco Chemical Corporation.

Dimethylstearylbenzyl ammonium chloride is sold under the trade names Varisoft® SDC by Witco Chemical Company and Ammonyx® 490 by Onyx Chemical Company.

B)-Amine Fabric Softening Active Compound

Suitable amine fabric softening compounds for use herein, which may be in amine form or cationic form are selected from:

(i)-Reaction products of higher fatty acids with a polyamine selected from the group consisting of hydroxyalkylalkylenediamines and dialkylenetriamines and mixtures thereof. These reaction products are mixtures of several compounds in view of the multi-functional structure of the polyamines.

The preferred Component (i) is a nitrogenous compound selected from the group consisting of the reaction product mixtures or some selected components of the mixtures.

One preferred component (i) is a compound selected from the group consisting of substituted imidazoline compounds having the formula:

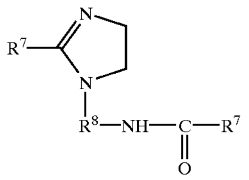

wherein $R^7$ is an acyclic aliphatic $C_{15}$–$C_{21}$ hydrocarbon group and $R^8$ is a divalent $C_1$–$C_3$ alkylene group.

Component (i) materials are commercially available as: Mazamide® 6, sold by Mazer Chemicals, or Ceranine® HC, sold by Sandoz Colors & Chemicals; stearic hydroxyethyl imidazoline sold under the trade names of Alkazine® ST by Alkaril Chemicals, Inc., or Schercozoline® S by Scher Chemicals, Inc.; N,N"-ditallowalkoyidiethylenetriamine; 1-tallowamidoethyl-2-tallowimidazoiine (wherein in the preceding structure $R^1$ is an aliphatic $C_{15}$–$C_{17}$ hydrocarbon group and $R^8$ is a divalent ethylene group).

Certain of the Components (i) can also be first dispersed in a Bronsted acid dispersing aid having a pKa value of not greater than 4; provided that the pH of the final composition is not greater than 6. Some preferred dispersing aids are hydrochloric acid, phosphoric acid, or methylsulfonic acid.

Both N,N"-ditallowalkoyldiethylenetriamine and 1-tallow(amidoethyl)-2-tallowimidazoline are reaction products of tallow fatty acids and diethylenetriamine, and are precursors of the cationic fabric softening agent methyl-1-tallowamidoethyl-2-tallowimidazolinium methylsulfate (see "Cationic Surface Active Agents as Fabric Softeners," R. R. Egan, Journal of the American Oil Chemicals' Society, January 1978, pages 118–121). N,N"-ditallow alkoyldiethylenetriamine and 1-tallowamidoethyl-2-tallowimidazoline can be obtained from Witco Chemical Company as experimental chemicals. Methyl-1-tallowamidoethyl-2-tallowimidazolinium methylsulfate is sold by Witco Chemical Company under the tradename Varisoft® 475.

(ii)-softener having the formula:

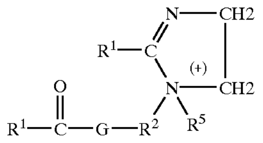

wherein each $R^2$ is a $C_{1-6}$ alkylene group, preferably an ethylene group; and G is an oxygen atom or an —NR— group; and each R, $R^1$, $R^2$ and $R^5$ have the definitions given above and $A^-$ has the definitions given above for $X^-$.

An example of Compound (ii) is 1-oleylamidoethyl-2-oleylimidazolinium chloride wherein $R^1$ is an acyclic aliphatic $C_{15}$–$C_{17}$ hydrocarbon group, $R^2$ is an ethylene group, G is a NH group, $R^5$ is a methyl group and $A^-$ is a chloride anion.

(iii)-softener having the formula:

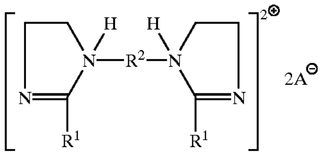

wherein R, $R^1$, $R^2$, and $A^-$ are defined as above.

An example of Compound (iii) is the compound having the formula:

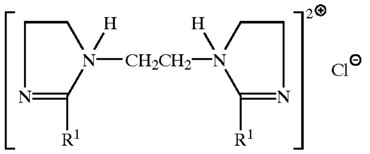

wherein $R^1$ is derived from oleic acid.

Additional fabric softening materials may be used in addition or alternatively to the cationic fabric softener. These may be selected from nonionic, amphoteric or anionic fabric softening material. Disclosure of such materials may be found in U.S. Pat. Nos. 4,327,133; 4,421,792; 4,426,299; 4,460,485; 3,644,203; 4,661,269; 4,439,335; 3,861,870; 4,308,151; 3,886,075; 4,233,164; 4,401,578; 3,974,076; 4,237,016 and EP 472,178.

Typically, such nonionic fabric softener materials have an HLB of from 2 to 9, more typically from 3 to 7. Such nonionic fabric softener materials tend to be readily dispersed either by themselves, or when combined with other materials such as single-long-chain alkyl cationic surfactant described in detail hereinafter. Dispersibility can be improved by using more single-long-chain alkyl cationic surfactant, mixture with other materials as set forth hereinafter, use of hotter water, and/or more agitation. In general, the materials selected should be relatively crystalline, higher melting, (e.g. >40° C.) and relatively water-insoluble.

Preferred nonionic softeners are fatty acid partial esters of polyhydric alcohols, or anhydrides thereof, wherein the alcohol, or anhydride, contains from 2 to 18, preferably from 2 to 8, carbon atoms, and each fatty acid moiety contains from 12 to 30, preferably from 16 to 20, carbon atoms. Typically, such softeners contain from one to 3, preferably 2 fatty acid groups per molecule.

The polyhydric alcohol portion of the ester can be ethylene glycol, glycerol, poly (e.g., di-, tri-, tetra, penta-, and/or hexa-) glycerol, xylitol, sucrose, erythritol, pentaerythritol, sorbitol or sorbitan. Sorbitan esters and polyglycerol monostearate are particularly preferred.

The fatty acid portion of the ester is normally derived from fatty acids having from 12 to 30, preferably from 16 to 20, carbon atoms, typical examples of said fatty acids being lauric acid, myristic acid, palmitic acid, stearic acid and behenic acid. Highly preferred optional nonionic softening agents for use in the present invention are the sorbitan esters, which are esterified dehydration products of sorbitol, and the glycerol esters.

Commercial sorbitan monostearate is a suitable material. Mixtures of sorbitan stearate and sorbitan palmitate having stearate/palmitate weight ratios varying between 10:1 and 1:10, and 1,5-sorbitan esters are also useful.

Glycerol and polyglycerol esters, especially glycerol, diglycerol, triglycerol, and polyglycerol mono- and/or di-esters, preferably mono-, are preferred herein (e.g. polyglycerol monostearate with a trade name of Radiasurf 7248).

Useful glycerol and polyglycerol esters include monoesters with stearic, oleic, palmitic, lauric, isostearic, myristic, and/or behenic acids and the diesters of stearic, oleic, palmitic, lauric, isostearic, behenic, and/or myristic acids. It is understood that the typical mono-ester contains some di- and tri-ester, etc.

The "glycerol esters" also include the polyglycerol, e.g., diglycerol through octaglycerol esters. The polyglycerol polyols are formed by condensing glycerin or epichlorohydrin together to link the glycerol moieties via ether linkages. The mono- and/or diesters of the polyglycerol polyols are preferred, the fatty acyl groups typically being those described herein before for the sorbitan and glycerol esters.

Further fabric softening components suitable for use herein are the softening clays, such as the low ion-exchange-capacity ones described in EP-A-0,150,531.

Of course, the term "softening active" can also encompass mixed softening active agents.

Preferred among the classes of softener compounds disclosed herein before are the diester or diamido quaternary ammonium fabric softening active compound (DEQA).

The fabric softener compounds herein are present at levels of from 1% to 80% of compositions herein, depending on the composition execution which can be dilute with a preferred level of active from 5% to 15%, or concentrated, with a preferred level of active from 15% to 50%, most preferably 15% to 35% by weight of the composition.

Fully formulated softening compositions preferably contain, in addition to the herein before described components, one or more of the following ingredients.

(A) Brighteners

The compositions herein can also optionally contain from 0.005% to 5% by weight of certain types of hydrophilic optical brighteners which also provide a dye transfer inhibition action. If used, the compositions herein will preferably comprise from 0.001% to 1% by weight of such optical brighteners. The hydrophilic optical brighteners useful in the present invention are those having the structural formula:

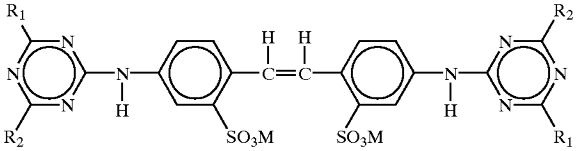

wherein $R_1$ is selected from anilino, N-2-bis-hydroxyethyl and NH-2-hydroxyethyl; $R_2$ is selected from N-2-bis-hydroxyethyl, N-2-hydroxyethyl-N-methylamino, morphilino, chloro and amino; and M is a salt-forming cation such as sodium or potassium.

When in the above formula, $R_1$ is anilino, $R_2$ is N-2-bis-hydroxyethyl and M is a cation such as sodium, the brightener is 4,4',-bis[(4-anilino-6-(N-2-bis-hydroxyethyl)-s-triazine-2-yl)amino]-2,2'-stilbenedisulfonic acid and disodium salt. This particular brightener species is commercially marketed under the tradename Tinopal-UNPA-GX® by Ciba-Geigy Corporation. Tinopal-UNPA-GX is the preferred hydrophilic optical brightener useful in the rinse added compositions herein.

When in the above formula, $R_1$ is anilino, $R_2$ is N-2-hydroxyethyl-N-2-methylamino and M is a cation such as sodium, the brightener is 4,4'-bis[(4-anilino-6-(N-2-hydroxyethyl-N-methylamino)-s-triazine-2-yl)amino]2,2'-stilbenedisulfonic acid disodium salt. This particular brightener species is commercially marketed under the tradename Tinopal 5BM-GX® by Ciba-Geigy Corporation.

When in the above formula, $R_1$ is anilino, $R_2$ is morphilino and M is a cation such as sodium, the brightener is 4,4'-bis[(4-anilino-6-morphilino-s-triazine-2 -yl)amino]2,2'-stilbenedisulfonic acid, sodium salt. This particular brightener species is commercially marketed under the tradename Tinopal AMS-GX® by Ciba Geigy Corporation.

(B) Dispersibility Aids

Relatively concentrated compositions containing both saturated and unsaturated diester quaternary ammonium compounds can be prepared that are stable without the addition of concentration aids. However, the compositions of the present invention may require organic and/or inorganic concentration aids to go to even higher concentrations and/or to meet higher stability standards depending on the other ingredients. These concentration aids which typically can be viscosity modifiers may be needed, or preferred, for ensuring stability under extreme conditions when particular softener active levels are used. The surfactant concentration aids are typically selected from the group consisting of (1) single long chain alkyl cationic surfactants; (2) nonionic surfactants; (3) amine oxides; (4) fatty acids; and (5) mixtures thereof. These aids are described in WO 94/20597, specifically on page 14, line 12 to page 20, line 12, which is herein incorporated by reference.

When said dispersibility aids are present, the total level is from 2% to 25%, preferably from 3% to 17%, more preferably from 4% to 15%, and even more preferably from 5% to 13% by weight of the composition. These materials can either be added as part of the active softener raw material, (I), e.g., the mono-long chain alkyl cationic surfactant and/or the fatty acid which are reactants used to form the biodegradable fabric softener active as discussed herein before, or added as a separate component. The total level of dispersibility aid includes any amount that may be present as part of component (I).

(1) Mono-Alkyl Cationic Quaternary Ammonium Compound

When the mono-alkyl cationic quaternary ammonium compound is present, it is typically present at a level of from 2% to 25%, preferably from 3% to 17%, more preferably from 4% to 15%, and even more preferably from 5% to 13% by weight of the composition, the total mono-alkyl cationic quaternary ammonium compound being at least at an effective level.

Such mono-alkyl cationic quaternary ammonium compounds useful in the present invention are, preferably, quaternary ammonium salts of the general formula:

$$[R^4N^+(R^5)_3]X^-$$

wherein $R^4$ is $C_8$–$C_{22}$ alkyl or alkenyl group, preferably $C_{10}$–$C_{18}$ alkyl or alkenyl group; more preferably $C_{10}$–$C_{14}$ or $C_{16}$–$C_{18}$ alkyl or alkenyl group;

each $R^5$ is a $C_1$–$C_6$ alkyl or substituted alkyl group (e.g., hydroxy alkyl), preferably $C_1$–$C_3$ alkyl group, e.g., methyl (most preferred), ethyl, propyl, and the like, a benzyl group, hydrogen, a polyethoxylated chain with from 2 to 20 oxyethylene units, preferably from 2.5 to 13 oxyethylene units, more preferably from 3 to 10 oxyethylene units, and mixtures thereof; and $X^-$ is as defined herein before for (Formula (I)).

Especially preferred dispersibility aids are monolauryl trimethyl ammonium chloride and monotallow trimethyl ammonium chloride available from Witco under the trade names Adogen® 412 and Adogen® 471, monooleyl or monocanola trimethyl ammonium chloride available from Witco under the tradename Adogen® 417, monococonut trimethyl ammonium chloride available from Witco under the trade name Adogen® 461, and monosoya trimethyl ammonium chloride available from Witco under the trade name Adogen® 415. The $R^4$ group can also be attached to the cationic nitrogen atom through a group containing one, or more, ester, amide, ether, amine, etc., linking groups which can be desirable for increased concentratability of component (I), etc. Such linking groups are preferably within from one to three carbon atoms of the nitrogen atom.

Mono-alkyl cationic quaternary ammonium compounds also include $C_8$–$C_{22}$ alkyl choline esters. The preferred dispersibility aids of this type have the formula:

$$R^1C(O)—O—CH_2CH_2N^+(R)_3X^-$$

wherein $R^1$, R and $X^-$ are as defined previously.

Highly preferred dispersibility aids include $C_{12}$–$C_{14}$ coco choline ester and $C_{16}$–$C_{18}$ tallow choline ester.

Suitable biodegradable single-long-chain alkyl dispersibility aids containing an ester linkage in the long chains are described in U.S. Pat. No. 4,840,738, said patent being incorporated herein by reference.

When the dispersibility aid comprises alkyl choline esters, preferably the compositions also contain a small amount, preferably from 2% to 5% by weight of the composition, of organic acid. Organic acids are described in EP404,471, which is herein incorporated by reference. Preferably the organic acid is selected from the group consisting of glycolic acid, acetic acid, citric acid, and mixtures thereof.

Ethoxylated quaternary ammonium compounds which can serve as the dispersibility aid include ethylbis (polyethoxy ethanol)alkylammonium ethyl-sulfate with 17 moles of ethylene oxide, available under the trade name Variquat® 66 from Witco Corporation; polyethylene glycol (15) oleammonium chloride, available under the trade name Ethoquad® 0/25 from Akzo; and polyethylene glycol (15) cocomonium chloride, available under the trade name Ethoquad® C/25 from Akzo.

Quatemary compounds having only a single long alkyl chain, can protect the cationic softener from interacting with anionic surfactants and/or detergent builders that are carried over into the rinse from the wash solution.

(2) Nonionic Surfactant (Alkoxylated Materials)

Suitable nonionic surfactants to serve as the viscosity/dispersibility modifier include addition products of ethylene oxide and, optionally, propylene oxide, with fatty alcohols, fatty acids, fatty amines, etc. They are referred to herein as ethoxylated fatty alcohols, ethoxylated fatty acids, and ethoxylated fatty amines. Any of the alkoxylated materials of the particular type described hereinafter can be used as the nonionic surfactant. In general terms, the nonionics herein, when used alone, in liquid compositions are at a level of from 0% to 5%, preferably from 0.1% to 5%, more preferably from 0.2% to 3%. Suitable compounds are substantially water-soluble surfactants of the general formula:

$$R^2—Y—(C_2H_4O)_z—C_2H_4OH$$

wherein $R^2$ for both solid and liquid compositions is selected from the group consisting of primary, secondary and branched chain alkyl and/or acyl hydrocarbyl groups; primary, secondary and branched chain alkenyl hydrocarbyl groups; and primary, secondary and branched chain alkyl- and alkenyl-substituted phenolic hydrocarbyl groups; said hydrocarbyl groups having a hydrocarbyl chain length of from 8 to 20, preferably from 10 to 18 carbon atoms. More preferably the hydrocarbyl chain length for liquid compositions is from 16 to 18 carbon atoms and for solid compositions from 10 to 14 carbon atoms. In the general formula for the ethoxylated nonionic surfactants herein, Y is typically —O—, —C(O)O—, —C(O)N(R)—, or —C(O)N(R) R—, preferably —O—, and in which $R^2$, and R, when present, have the meanings given herein before, and/or R can be hydrogen, and z is at least 8, preferably at least 10–11. Performance and, usually, stability of the softener composition decrease when fewer ethoxylate groups are present.

The nonionic surfactants herein are characterized by an HLB (hydrophilic-lipophilic balance) of from 7 to 20, preferably from 8 to 15. Of course, by defining $R^2$ and the number of ethoxylate groups, the HLB of the surfactant is, in general, determined. However, it is to be noted that the nonionic ethoxylated surfactants useful herein, for concentrated liquid compositions, contain relatively long chain $R^2$ groups and are relatively highly ethoxylated. While shorter alkyl chain surfactants having short ethoxylated groups can possess the requisite HLB, they are not as effective herein. Nonionic surfactants as the viscosity/dispersibility modifiers are preferred over the other modifiers disclosed herein for compositions with higher levels of perfume.

Examples of nonionic surfactants follow. The nonionic surfactants of this invention are not limited to these examples. In the examples, the integer defines the number of ethoxy (EO) groups in the molecule.

(3) Amine Oxides

Suitable amine oxides include those with one alkyl or hydroxyalkyl moiety of 8 to 22 carbon atoms, preferably from 10 to 18 carbon atoms, more preferably from 8 to 14 carbon atoms, and two alkyl moieties selected from the group consisting of alkyl groups and hydroxyalkyl groups with 1 to 3 carbon atoms.

Examples include dimethyloctylamine oxide, diethyidecylamine oxide, bis-(2-hydroxyethyl)dodecyl-amine oxide, dimethyldodecylamine oxide, dipropyltetradecylamine oxide, methylethylhexadecylamine oxide, dimethyl-2-hydroxyoctadecylamine oxide, and coconut fatty alkyl dimethylamine oxide.

(C) Stabilizers

Stabilizers can be present in the compositions of the present invention. The term "stabilizer," as used herein, includes antioxidants and reductive agents. These agents are present at a level of from 0% to 2%, preferably from 0.01% to 0.2%, more preferably from 0.035% to 0.1% for antioxidants, and more preferably from 0.01% to 0.2% for reductive agents. These assure good odor stability under long term storage conditions. Antioxidants and reductive agent stabilizers are especially critical for unscented or low scent products (no or low perfume).

Examples of antioxidants that can be added to the compositions of this invention include a mixture of ascorbic acid, ascorbic palmitate, propyl gallate, available from Eastman Chemical Products, Inc., under the trade names Tenox® PG and Tenox® S-1; a mixture of BHT (butylated hydroxytoluene), BHA (butylated hydroxyanisole), propyl gallate, and citric acid, available from Eastman Chemical Products, Inc., under the trade name Tenox®-6; butylated hydroxytoluene, available from UOP Process Division under the trade name Sustane® BHT; tertiary butylhydroquinone, Eastman Chemical Products, Inc., as Tenox® TBHQ; natural tocopherols, Eastman Chemical Products, Inc., as Tenoxe GT-1/GT-2; and butylated hydroxyanisole, Eastman Chemical Products, Inc., as BHA; long chain esters ($C_8$–$C_{22}$) of gallic acid, e.g., dodecyl gallate; Irganox® 1010; Irganox® 1035; Irganox® B 1171; Irganox® 1425; Irganox® 3114; Irganox® 3125; and mixtures thereof; preferably Irganox® 3125, Irganox® 1425, Irganox® 3114, and mixtures thereof; more preferably Irganox® 3125 alone or mixed with citric acid and/or other chelators such as isopropyl citrate, Dequest® 2010, available from Monsanto with a chemical name of 1-hydroxyethylidene-1,1-diphosphonic acid (etidronic acid), and Tiron®, available from Kodak with a chemical name of 4,5-dihydroxy-m-benzene-sulfonic acid/sodium salt, and DTPA®, available from Aldrich with a chemical name of diethylenetriaminepentaacetic acid.

(D) Soil Release Agent

In the present invention, an optional soil release agent can be added. Typical levels of incorporation in the composition are from 0% to 10%, preferably from 0.2% to 5%, of a soil release agent. Preferably, such a soil release agent is a polymer.

Soil Release agents are desirably used in fabric softening compositions of the instant invention. Any polymeric soil release agent known to those skilled in the art can optionally be employed in the compositions of this invention. Polymeric soil release agents are characterized by having both hydrophilic segments, to hydrophilize the surface of hydrophobic fibers, such as polyester and nylon, and hydrophobic segments, to deposit upon hydrophobic fibers and remain adhered thereto through completion of washing and rinsing cycles and, thus, serve as an anchor for the hydrophilic segments. This can enable stains occurring subsequent to treatment with the soil release agent to be more easily cleaned in later washing procedures.

If utilized, soil release agents will generally comprise from about 0.01% to about 10.0%, by weight, of the detergent compositions herein, typically from about 0.1% to about 5%, preferably from about 0.2% to about 3.0%.

The following, all included herein by reference, describe soil release polymers suitable for use in the present invention. U.S. Pat. No. 3,959,230 Hays, issued May 25, 1976; U.S. Pat. No. 3,893,929 Basadur, issued Jul. 8, 1975; U.S. Pat. No. 4,000,093, Nicol, et al., issued Dec. 28, 1976; U.S. Pat. No. 4,702,857 Gosselink, issued Oct. 27, 1987; U.S. Pat. No. 4,968,451, Scheibel et al., issued November 6; U.S. Pat. No. 4,702,857, Gosselink, issued Oct. 27, 1987; U.S. Pat. No. 4,711,730, Gosselink et al., issued Dec. 8, 1987; U.S. Pat. No. 4,721,580, Gosselink, issued Jan. 26, 1988; U.S. Pat. No. 4,877,896, Maldonado et al., issued Oct. 31, 1989; U.S. Pat. No. 4,956,447, Gosselink et al., issued Sep. 11, 1990; U.S. Pat. No. 5,415,807 Gosselink et al., issued May 16, 1995; European Patent Application 0 219 048, published Apr. 22, 1987 by Kud, et al..

Further suitable soil release agents are described in U.S. Pat. No. 4,201,824, Violland et al.; U.S. Pat. No. 4,240,918 Lagasse et al.; U.S. Pat. No. 4,525,524 Tung et al.; U.S. Pat. No. 4,579,681, Ruppert et al.; U.S. Pat. No. 4,240,918; U.S. Pat. No. 4,787,989; U.S. Pat. No. 4,525,524; EP 279,134 A, 1988, to Rhone-Poulenc Chemie; EP 457,205 A to BASF (1991); and DE 2,335,044 to Unilever N. V., 1974 all incorporated herein by reference.

Commercially available soil release agents include the METOLOSE SM100, METOLOSE SM200 manufactured by Shin-etsu Kagaku Kogyo K.K., SOKALAN type of material, e.g., SOKALAN HP-22, available from BASF (Germany), ZELCON 5126 (from Dupont) and MILEASE T (from ICI).

(E) Scum Dispersant

In the present invention, the premix can be combined with an optional scum dispersant, other than the soil release agent, and heated to a temperature at or above the melting point(s) of the components.

The preferred scum dispersants herein are formed by highly ethoxylating hydrophobic materials. The hydrophobic material can be a fatty alcohol, fatty acid, fatty amine, fatty acid amide, amine oxide, quaternary ammonium compound, or the hydrophobic moieties used to form soil release polymers. The preferred scum dispersants are highly ethoxylated, e.g., more than 17, preferably more than 25, more preferably more than 40, moles of ethylene oxide per molecule on the average, with the polyethylene oxide portion being from 76% to 97%, preferably from 81% to 94%, of the total molecular weight.

The level of scum dispersant is sufficient to keep the scum at an acceptable, preferably unnoticeable to the consumer, level under the conditions of use, but not enough to adversely affect softening. For some purposes it is desirable that the scum is nonexistent. Depending on the amount of anionic or nonionic detergent, etc., used in the wash cycle of a typical laundering process, the efficiency of the rinsing steps prior to the introduction of the compositions herein, and the water hardness, the amount of anionic or nonionic detergent surfactant and detergency builder (especially phosphates and zeolites) entrapped in the fabric (laundry) will vary. Normally, the minimum amount of scum dispersant should be used to avoid adversely affecting softening properties. Typically scum dispersion requires at least 2%, preferably at least 4% (at least 6% and preferably at least 10% for maximum scum avoidance) based upon the level of softener active. However, at levels of 10% (relative to the softener material) or more, one risks loss of softening efficacy of the product especially when the fabrics contain high proportions of nonionic surfactant which has been absorbed during the washing operation.

Preferred scum dispersants are: Brij 700®; Varonic U-250®; Genapol T-500®, Genapol T-800®; Plurafac A-79®; and Neodol 25-50®.

(F) Bactericides

Examples of bactericides used in the compositions of this invention include glutaraldehyde, formaldehyde, 2-bromo-2-nitro-propane-1,3-diol sold by Inolex Chemicals, located in Philadelphia, Pa., under the trade name Bronopol®, and a mixture of 5-chloro-2-methyl-4-isothiazoline-3-one and 2-methyl-4-isothiazoline-3-one sold by Rohm and Haas Company under the trade name Kathon 1 to 1,000 ppm by weight of the agent.

(G) Perfume

The present invention can contain any softener compatible perfume. Suitable perfumes are disclosed in U.S. Pat. No. 5,500,138, said patent being incorporated herein by reference.

As used herein, perfume includes fragrant substance or mixture of substances including natural (i.e., obtained by extraction of flowers, herbs, leaves, roots, barks, wood, blossoms or plants), artificial (i.e., a mixture of different nature oils or oil constituents) and synthetic (i.e., synthetically produced) odoriferous substances. Such materials are often accompanied by auxiliary materials, such as fixatives, extenders, stabilizers and solvents. These auxiliaries are also included within the meaning of "perfume", as used herein. Typically, perfumes are complex mixtures of a plurality of organic compounds.

Examples of perfume ingredients useful in the perfumes of the present invention compositions include, but are not limited to, hexyl cinnamic aldehyde; amyl cinnamic aldehyde; amyl salicylate; hexyl salicylate; terpineol; 3,7-dimethyl-cis-2,6-octadien-1-ol; 2,6-dimethyl-2-octanol; 2,6-dimethyl-7-octen-2-ol; 3,7-dimethyl-3-octanol; 3,7-dimethyl-trans-2,6-octadien-1-ol; 3,7-dimethyl-6-octen-1-ol; 3,7-dimethyl-1-octanol; 2-methyl-3-(para-tert-butylphenyl)-propion-aldehyde; 4-(4-hydroxy-4-methylpentyl)-3-cyclohexene-1-carbox-aldehyde; tricyclodecenyl propionate; tricyclodecenyl acetate; anisaldehyde; 2-methyl-2-(para-iso-propylphenyl)-propionaldehyde; ethyl-3-methyl-3-phenyl glycidate; 4-(para-hydroxyphenyl)-butan-2-one; 1-(2,6,6-trimethyl-2-cyclohexen-1-yl)-2-buten-1-one; para-methoxyacetophenone; para-methoxy-alpha-phenylpropene; methyl-2-n-hexyl-3-oxo-cyclopentane carboxylate; undecalactone gamma.

Additional examples of fragrance materials include, but are not limited to, orange oil; lemon oil; grapefruit oil; bergamot oil; clove oil; dodecalactone gamma; methyl-2-(2-pentyl-3-oxo-cyclopentyl) acetate; beta-naphthol methylether; methyl-beta-naphthylketone; coumarin; decylaldehyde; benzaldehyde; 4-tert-butylcyclohexyl acetate; alpha, alpha-dimethylphenethyl acetate; methylphenylcarbinyl acetate; Schiffs base of 4-(4-hydroxy-4-methylpentyl)-3-cyclohexene-1-carboxaldehyde and methyl anthranilate; cyclic ethyleneglycol diester of tridecandioic acid; 3,7-dimethyl-2,6-octadiene-1-nitrile; ionone gamma methyl; ionone alpha; ionone beta; petitgrain; methyl cedrylone; 7-acetyl-1,2,3,4,5,6,7,8-octahydro-1,1,6,7-tetramethyl-naphthalene; ionone methyl; methyl-1,6,10-trimethyl-2,5,9-cyclododecatrien-1-yl ketone; 7-acetyl-1,1,3,4,4,6-hexamethyl tetralin; 4-acetyl-6-tert-butyl-1,1-dimethyl indane; benzophenone; 6-acetyl-1,1,2,3,3,5-hexamethyl indane; 5-acetyl-3-isopropyl-1,1,2,6-tetramethyl indane; 1-dodecanal; 7-hydroxy-3,7-dimethyl octanal; 10-undecen-1-al; iso-hexenyl cyclohexyl carboxaldehyde; formyl tricyclodecan; cyclopentadecanolide; 16-hydroxy-9-hexadecenoic acid lactone; 1,3,4,6,7,8-hexahydro4,6,6,7,8,8-hexamethylcyclopenta-gamma-2-benzopyrane; ambroxane; dodecahydro-3a,6,6,9a-tetramethyinaphtho-[2,1b]furan; cedrol; 5-(2,2,3-trimethylcyclopent-3-enyl)-3-methylpentan-2-ol; 2-ethyl-4-(2,2,3-trimethyl-3-cyclopenten-1-yl)-2-buten-1-ol; caryophyllene alcohol; cedryl acetate; para-tert-butylcyclohexyl acetate; patchouli; olibanum resinoid; labdanum; vetivert; copaiba balsam; fir balsam; and condensation products of: hydroxycitronellal and methyl anthranilate; hydroxycitronellal and indol; phenyl acetaldehyde and indol; 4-(4-hydroxy4-methyl pentyl)-3-cyclohexene-1-carboxaldehyde and methyl anthranilate.

More examples of perfume components are geraniol; geranyl acetate; linalool; linalyl acetate; tetrahydrolinalool; citronellol; citronellyl acetate; dihydromyrcenol; dihydromyrcenyl acetate; tetrahydromyrcenol; terpinyl acetate; nopol; nopyl acetate; 2-phenylethanol; 2-phenylethyl acetate; benzyl alcohol; benzyl acetate; benzyl salicylate; benzyl benzoate; styrallyl acetate; dimethylbenzylcarbinol; trichloromethylphenylcarbinyl methylphenylcarbinyl acetate; isononyl acetate; vetiveryl acetate; vetiverol; 2-methyl-3-(p-tert-butylphenyl)-propanal; 2-methyl-3-(p-isopropylphenyl)-propanal; 3-(p-tert-butylphenyl)-propanal; 4-(4-methyl-3-pentenyl)-3-cyclohexenecarbaldehyde; 4-acetoxy-3-pentyltetrahydropyran; methyl dihydrojasmonate; 2-n-heptylcyclopentanone; 3-methyl-2-pentyl- cyclopentanone; n-decanal; n-dodecanal; 9-decenol-1; phenoxyethyl isobutyrate; phenylacetaldehyde dimethylacetal; phenylacetaldehyde diethylacetal; geranonitrile; citronellonitrile; cedryl acetal; 3-isocamphylcyclohexanol; cedryl methylether; isolongifolanone; aubepine nitrile; aubepine; heliotropine; eugenol; vanillin; diphenyl oxide; hydroxycitronellal ionones; methyl ionones; isomethyl ionomes; irones; cis-3-hexenol and esters thereof; indane musk fragrances; tetralin musk fragrances; isochroman musk fragrances; macrocyclic ketones; macrolactone musk fragrances; ethylene brassylate.

The perfumes useful in the present invention compositions are substantially free of halogenated materials and nitromusks.

Suitable solvents, diluents or carriers for perfumes ingredients mentioned above are for examples, ethanol, isopropanol, diethylene glycol, monoethyl ether, dipropylene glycol, diethyl phthalate, triethyl citrate, etc. The amount of such solvents, diluents or carriers incorporated in the perfumes is preferably kept to the minimum needed to provide a homogeneous perfume solution.

Perfume can be present at a level of from 0% to 10%, preferably from 0.1% to 5%, and more preferably from 0.2% to 3%, by weight of the finished composition. Fabric softener compositions of the present invention provide improved fabric perfume deposition.

(H) Chelating Agents

The compositions and processes herein can optionally employ one or more copper and/or nickel chelating agents ("chelators"). Such water-soluble chelating agents can be selected from the group consisting of amino carboxylates, amino phosphonates, polyfunctionally-substituted aromatic chelating agents and mixtures thereof, all as hereinafter defined. The whiteness and/or brightness of fabrics are substantially improved or restored by such chelating agents and the stability of the materials in the compositions are improved. Without intending to be bound by theory, it is believed that the benefit of these materials is due in part to their exceptional ability to remove iron and manganese ions from washing solutions by formation of soluble chelates.

Amino carboxylates useful as optional chelating agents include ethylenediaminetetracetates, N-hydroxyethylethylenediaminetriacetates, nitrilo-triacetates, ethylenediamine tetraproprionates, triethylenetetra-aminehexacetates, diethylenetriaminepentaacetates, and ethanoldiglycines, alkali metal, ammonium, and substituted ammonium salts therein and mixtures therein.

Amino phosphonates are also suitable for use as chelating agents in the compositions of the invention when at least low levels of total phosphorus are permitted in detergent compositions, and include ethylenediaminetetrakis (methyienephosphonates) as DEQUEST. Preferred, these amino phosphonates do not contain alkyl or alkenyl groups with more than about 6 carbon atoms.

Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A preferred biodegradable chelator for use herein is ethylenediamine disuccinate ("EDDS"), especially the [S,S] isomer as described in U.S. Pat. No. 4,704,233, Nov. 3, 1987, to Hartman and Perkins.

The compositions herein may also contain water-soluble methyl glycine diacetic acid (MGDA) salts (or acid form) as a chelant or co-builder useful with, for example, insoluble builders such as zeolites, layered silicates and the like.

Preferred chelating agents include DETMP, DETPA, NTA, EDDS and mixtures thereof.

If utilized, these chelating agents will generally comprise from about 0.1% to about 15% by weight of the fabric care compositions herein. More preferably, if utilized, the chelating agents will comprise from about 0.1% to about 3.0% by weight of such compositions.

(I) Crystal Growth Inhibitor Component

The compositions of the present invention can further contain a crystal growth inhibitor component, preferably an organodiphosphonic acid component, incorporated preferably at a level of from 0.01% to 5%, more preferably from 0.1% to 2% by weight of the compositions.

By organo diphosphonic acid it is meant herein an organo diphosphonic acid which does not contain nitrogen as part of its chemical structure. This definition therefore excludes the organo aminophosphonates, which however may be included in compositions of the invention as heavy metal ion sequestrant components.

The organo diphosphonic acid is preferably a $C_1$–$C_4$ diphosphonic acid, more preferably a $C_2$ diphosphonic acid, such as ethylene diphosphonic acid, or most preferably ethane 1-hydroxy-1,1-diphosphonic acid (HEDP) and may be present in partially or fully ionized form, particularly as a salt or complex.

Still useful herein as crystal growth inhibitor is the organic monophosphonic acid.

Organo monophosphonic acid or one of its salts or complexes is also suitable for use herein as a CGI.

By organo monophosphonic acid it is meant herein an organo monophosphonic acid which does not contain nitrogen as part of its chemical structure. This definition therefore excludes the organo aminophosphonates, which however may be included in compositions of the invention as heavy metal ion sequestrants.

The organo monophosphonic acid component may be present in its acid form or in the form of one of its salts or complexes with a suitable counter cation. Preferably any salts/complexes are water soluble, with the alkali metal and alkaline earth metal salts/complexes being especially preferred.

A prefered organo monophosphonic acid is 2-phosphonobutane-1,2,4-tricarboxylic acid commercially available from Bayer under the tradename of Bayhibit.

(J)-Enzyme

The compositions and processes herein can optionally employ one or more enzymes such as lipases, proteases, cellulase, amylases and peroxidases. A preferred enzyme for use herein is a cellulase enzyme. Indeed, this type of enzyme will further provide a color care benefit to the treated fabric. Cellulases usable herein include both bacterial and fungal types, preferably having a pH optimum between 5 and 9.5. U.S. Pat. No. 4,435,307 discloses suitable fungal cellulases from *Humicola insolens* or Humicola strain DSM1800 or a cellulase 212-producing fungus belonging to the genus Aeromonas, and cellulase extracted from the hepatopancreas of a marine mollusk, *Dolabella Auricula Solander*. Suitable cellulases are also disclosed in GB-A-2.075.028; GB-A-2.095.275 and DE-OS-2.247.832. CAREZYMEO® and CELLUZYME® (Novo) are especially useful. Other suitable cellulases are also disclosed in WO 91/17243 to Novo, WO 96/34092, WO 96/34945 and EP-A-0,739,982. In practical terms for current commercial preparations, typical amounts are up to 5 mg by weight, more typically 0.01 mg to 3 mg, of active enzyme per gram of the detergent composition. Stated otherwise, the compositions herein will typically comprise from 0.001% to 5%, preferably 0.01%–1% by weight of a commercial enzyme preparation. In the particular cases where activity of the enzyme preparation can be defined otherwise such as with cellulases, corresponding activity units are preferred (e.g. CEVU or cellulase Equivalent Viscosity Units). For instance, the compositions of the present invention can contain cellulase enzymes at a level equivalent to an activity from 0.5 to 1000

CEVU/gram of composition. Cellulase enzyme preparations used for the purpose of formulating the compositions of this invention typically have an activity comprised between 1,000 and 10,000 CEVU/gram in liquid form, around 1,000 CEVU/gram in solid form.

(K) Liquid Carrier

Another optional, but preferred, ingredient is a liquid carrier. The liquid carrier employed in the instant compositions is preferably at least primarily water due to its low cost, relative availability, safety, and environmental compatibility. The level of water in the liquid carrier is preferably at least 50%, most preferably at least 60%, by weight of the carrier. Mixtures of water and low molecular weight, e.g., <200, organic solvent, e.g., lower alcohols such as ethanol, propanol, isopropanol or butanol are useful as the carrier liquid. Low molecular weight alcohols include monohydric, dihydric (glycol, etc.) trihydric (glycerol, etc.), and higher polyhydric (polyols) alcohols.

(L) Other Optional Ingredients

The present invention can include optional components conventionally used in textile treatment compositions, for example: colorants; preservatives; surfactants; anti-shrinkage agents; fabric crisping agents; spotting agents; germicides; fungicides; anti-oxidants such as butylated hydroxy toluene, anti-corrosion agents, enzyme stabilisers, materials effective for inhibiting the transfer of dyes from one fabric to another during the cleaning process (i.e., dye transfer inhibiting agents), hydrotropes, processing aids, dyes or pigments, and the like.

The present invention can also include other compatible ingredients, including those as disclosed in WO96/02625, WO96121714, and WO96/21715.

Form of the Composition

The composition of the invention may take a variety of physical form including liquid, gel, foam in either aqueous or non-aqueous form, granular and tablet forms.

When in a liquid form, the composition may also be dispensed by a dispensing means such as a spray dispenser, or aerosol dispenser.

Spray Dispenser

The present invention also relates to such compositions incorporated into a spray dispenser to create an article of manufacture that can facilitate treatment of fabric articles and/or surfaces with said compositions containing the amine reaction product and other ingredients (examples are cyclodextrins, polysaccharides, polymers, surfactant, perfume, softener) at a level that is effective, yet is not discernible when dried on the surfaces. The spray dispenser comprises manually activated and non-manual powered (operated) spray means and a container containing the treating composition. Typical disclosure of such spray dispenser can be found in WO 96/04940 page 19 line 21 to page 22 line 27. The articles of manufacture preferably are in association with instructions for use to ensure that the consumer applies sufficient ingredient of the composition to provide the desired benefit. Typical compositions to be dispensed from a sprayer contain a level of amine reaction product of from about 0.01% to about 5%, preferably from about 0.05% to about 2%, more preferably from about 0.1% to about 1%, by weight of the usage composition.

Method of Use

Also provided herein is a method for providing a delayed release of an active ketone or aldehyde which comprises the step of contacting the surface to be treated with a compound or composition of the invention, and thereafter subjecting the treated surface with a material, preferably an aqueous medium like moisture or any other means susceptible of releasing the active from the amine reaction product.

By "surface", it is meant any surface onto which the compound can deposit. Typical examples of such material are fabrics, hard surfaces such as dishware, floors, bathrooms, toilet, kitchen, skin, and other surfaces in need of a delayed release of an active ketone or aldehyde such as that with litter like animal litter. Preferably, the surface is a fabric.

By "delayed release" is meant release of the active component (e.g perfume) over a longer period of time than by the use of the active (e.g., perfume) itself.

Abbreviations Used in the Following Invention Composition Examples

In the composition examples, the abbreviated component identifications have the following meanings:

| | |
|---|---|
| DEQA: | Di-(tallowyl-oxy-ethyl) dimethyl ammonium chloride |
| DTDMAC: | Ditallow dimethylammonium chloride |
| DEQA (2): | Di-(soft-tallowyloxyethyl) hydroxyethyl methyl ammonium methylsulfate. |
| DTDMAMS: | Ditallow dimethyl ammonium methylsulfate. |
| SDASA: | 1:2 ratio of stearyldimethyl amine:triple-pressed stearic acid. |
| Fatty acid: | Stearic acid of IV = 0 |
| Electrolyte: | Calcium chloride |
| PEG: | Polyethylene Glycol 4000 |
| Neodol 45-13: | C14–C15 linear primary alcohol ethoxylate, sold by Shell Chemical CO. |
| Cellulase: | Cellulytic enzyme sold under the tradename Carezyme, Celluzyme and/or Endolase by Novo Nordisk A/S. |
| Silicone antifoam: | Polydimethylsiloxane foam controller with siloxane-oxyalkylene copolymer as dispersing agent with a ratio of said foam controller to said dispersing agent of 10:1 to 100:1. |
| PEI: | Polyethyleneimine with an average molecular weight of 1800 and an average ethoxylation degree of 7 etholeneoxy residues per nitrogen |
| HEDP: | 1,1-hydroxyethane diphosphonic acid |
| ARP1: | Amine reaction product of ethyl 4-aminobenzoate with 2,4-dimethyl-3-cyclohexen-1-carboxaldehyde as made from Synthesis example I |
| ARP2: | Amine reaction product of aminobenzoic acid with 2,4-dimethyl-3-cyclohexen-1-carboxaldehyde made according to Synthesis example I |
| ARP3: | Amine reaction product of Lupasol P with α-Damascone as made from Synthesis example III |
| ARP4: | Amine reaction product of D-glucamine with Citronellal as made from Synthesis example II |
| ARP5: | Amine reaction product of LupasolHF with δ-Damascone as made from Synthesis example III |
| Polymer: | Polyvinylpyrroiidone K90 available from BASF under the tradename Luviskol K90 |
| Dye fixative: | Dye fixative commercially available from Clariant under the tradename Cartafix CB |
| Polyamine: | 1,4-Bis-(3-aminopropyl)piperazine |
| Bayhibit AM: | 2-Phosphonobutane-1,2,4-tricarboxylic acid commercially available from Bayer |
| Fabric softener active: | Di-(canoloyl-oxy-ethyl)hydroxyethyl methyl ammonium methylsulfate |
| HPBDC: | Hydroxypropyl beta-cyclodextrin |
| RAMEB: | Randomly methylated beta-cyclodextrin |
| Bardac 2050: | Dioctyl dimethyl ammonium chloride, 50% solution |
| Bardac 22250: | Didecyl dimethyl ammonium chloride, 50% solution |
| Genamin C100: | Coco fatty amine ethoxylated with 10 moles ethylene oxide and commercially available from Clariant |
| Genapol V4463: | Coco alcohol ethoxylated with 10 moles ethylene oxide and commercially available from Clariant |

-continued

| | |
|---|---|
| Silwet 7604: | Polyalkyleneoxide polysiloxanes of MW 4000 of formula R-$(CH_3)_2SiO-[(CH_3)_2SiO]_a-[(CH_3)(R)SiO]_b-Si(CH_3)_2$-R, wherein average a + b is 21, and commercially available from Osi Specialties, Inc., Danbury, Connecticut |
| Silwet 7600: | Polyalkyleneoxide polysiloxanes of MW 4000, of formula R-$(CH_3)_2SiO-[(CH_3)_2SiO]_a-[(CH_3)(R)SiO]_b-Si(CH_3)_2$-R, wherein average a + b is 11, and commercially available from Osi Specialties Inc., Danbury, Connecticut |

The following are synthesis examples of compounds according to the invention:

I-Synthesis of ethyl 4-aminobenzoate with 2.4-dimethyl-3-cyclohexen-1-carboxaldehyde To an ice cooled stirred solution of 10 g of 2,4-dimethyl-3-cyclohexen-1-carboxaldehyde (0.07 mol) in 35 mL EtOH and molecular sieves (4 Å, 20 g) 1 eq of the amine was added via an addition funnel. The reaction mixture was stirred under nitrogen atmosphere and protected from light. After 6 days the mixture was filtrated and the solvent was removed. The yield of imine formation is about 90%.

Similar results were obtained where the 2,4-dimethyl-3-cyclohexen-1-carboxaldehyde was replaced by bourgeonal, or trans-2-nonenal. Additionally, similar results were obtained where the ethyl-4-aminobenzoate was replaced by 4-amino benzoic acid.

II-Synthesis of D-glucamine with 2,4-dimethyl-3-cyclohexen-1-carboxaldehyde

To an ice cooled solution of 1 mmol D-glucamine in about 30 mL EtOH and molecular sieves (4 Å, 5 g) 1 eq of the 2,4-dimethyl-3-cyclohexen-1-carboxaldehyde was added. The reaction was stirred under nitrogen atmosphere and protected from light. After 3 to 4 days, the molecular sieves and the solvent were removed by filtration and evaporation respectively. The solid imine was obtained in 85 to 90% yield.

Similar results were obtained where the 2,4-dimethyl-3-cyclohexen-1-carboxaldehyde was replaced by citronellal, trans-2-nonenal, or decanal.

III-Synthesis of Lupasol with Damascone

The β-amino ketone from Lupasol G100 (commercial available by BASF content 50% water, 50% Lupasol G100 (Mw. 5000)) and α-Damascone was prepared using any one of these three different procedures described as follows:

1. Commercially available Lupasol G100 was dried using the following procedure: 20 g of the Lupasol solution was dried at the rotating evaporator during several hours. The obtained residue, still containing about 4.5 g of $H_2O$, was azeotropically distilled at the rotating evaporator using toluene. The residue was then placed in the desiccator dried at 60° C. (using $P_2O_5$ as water absorbing material). On basis of the obtained weight we concluded that the oil contained less then 10% $H_2O$. On basis of the NMR-spectra we concluded that this is probably less then 5%. This dried sample was then used in the preparation of β-amino ketones.

1.38 g of the dried Lupasol G100 was dissolved in 7 ml. ethanol. The solution was stirred gently with a magnetic stirrer during a few minutes before 2 g $Na_2SO_4$ (anhydrous) was added. After stirring again for a few minutes 2.21 g α-Damascone was added over a period of 1 minute. After two days reaction, the mixture was filtrated over a Celite filter (vide supra), and the residue washed thoroughly with ethanol. About 180 ml. of a light foaming filtrate was obtained. This was concentrated until dryness using a rotating evaporator and dried over $P_2O_5$ in an desiccator at room temperature. About 3.5 of a colorless oil was obtained.

2. 4.3 g Lupasol G100 solution was (without drying) dissolved in 10 ml. ethanol. The solution was stirred with a magnetic stirrer during a few minutes before 3.47 g α-Damascone was added over a 1.5 minutes period. After two days reaction at room temperature the reaction mixture was filtrated over Celite (vide supra) and the residue washed thoroughly with ethanol. The filtrate (200 ml., light foaming) was concentrated at the evaporator and dried in an desiccator ($P_2O_5$ as drying agent) at room temperature. About 6.0 g of a colorless oil was obtained.

3. To about 3.0 g of Lupasol G100 solution (used as such) was added 2.41 9 α-Damascone. The mixture was stirred without using solvent. After stirring for 4 days the obtained oil was dissolved in 100 ml. THF, dried with $MgSO_4$, filtrated and the filtrate concentrated at the rotating evaporator. After drying in the exsiccator ($P_2O_5$) at room temperature, about 4.1 g of a colorless oil was obtained. This oil still contained about 13% (w/w) of THF, even after a prolonged drying (3 days).

The product obtained from the three procedures had identical NMR-spectra.

The β-amino ketone from Lupasol P and α-Damascone was prepared using the procedure described as follows:

About 1.8 g Lupasol P solution (50% $H_2O$, 50% Lupasol Mw. 750000, as obtained from BASF) was dissolved in 7 ml ethanol, the solution was stirred for a few minutes with a magnetic stirrer before 1.44 g α-Damascone was added. After three days the reaction mixture was filtrated over a celite filter (vide supra) and the residue washed thoroughly with ethanol. After concentrating of the filtrate and drying of the obtained oil in the desiccator ($P_2O_5$) at room temperature, about 3 g of the reaction product between Lupasol and α-Damascone was obtained.

In the following formulation examples all levels are quoted as % by weight of the composition unless otherwise stated, and incorporation of the amine reaction product so called herein after "ARP" in the fully formulated composition is carried out by dry addition (d), encapsulation in starch (es) as described in GB-1,464,616 or cyclodextrin (ec) or as is in the composition as defined herein before. The term in bracket for the ARP in the formulation examples refers to the means of incorporation. When none is provided, the incorporation is made as it is. The levels given for the ARP, whether processed or not, refer to the level of ARP as is and not to the processed ARP.

EXAMPLE 1

The following fabric softening compositions are in accordance with the present invention

| Component | A | B | C | D | E | F | G | H |
|---|---|---|---|---|---|---|---|---|
| DTDMAC | — | — | — | — | — | 4.5 | 15.0 | 15.0 |
| DEQA | 2.6 | 2.9 | 18.0 | 18.0 | 19.0 | — | — | — |
| Fatty acid | 0.3 | — | 1.0 | 1.0 | — | — | — | — |
| HCl | 0.02 | 0.02 | 0.02 | 0.02 | 0.02 | 0.02 | 0.02 | 0.02 |
| PEG | — | — | 0.6 | 0.6 | 0.6 | — | 0.6 | 0.6 |
| Perfume | 1.0 | 1.0 | 1.0 | 1.0 | 1.0 | 1.0 | 1.0 | 1.0 |
| Silicone antifoam | 0.01 | 0.01 | 0.01 | 0.01 | 0.01 | 0.01 | 0.01 | 0.01 |
| ARP 5 | 0.3 | — | 0.2 | 0.2 | — | — | — | 0.2 |
| ARP 3 | — | 0.05 | — | — | 0.2 | — | 0.4 | 0.4 |
| ARP 4 | — | — | — | 0.02 | — | 0.05 | — | — |
| Electrolyte (ppm) | — | — | 600 | 600 | 1200 | — | 1200 | 1200 |
| Dye (ppm) | 10 | 10 | 50 | 50 | 50 | 10 | 50 | 50 |
| Water and minors to balance to 100% | | | | | | | | |

EXAMPLE 2

The following rinse added fabric softener composition was prepared according to the present invention:

| | A | B | C | D | E |
|---|---|---|---|---|---|
| DEQA (2) | 20.0 | 20.0 | 20.0 | 20.0 | 20.0 |
| ARP1 | 0.5 | — | — | — | — |
| ARP2 | — | 0.3 | | — | 0.04 |
| ARP3 | — | 0.1 | 0.1 | — | — |
| ARP4 | — | — | — | 0.1 | 0.1 |
| Cellulase | 0.001 | 0.001 | 0.001 | 0.001 | 0.001 |
| HCL | 0.03 | 0.03 | 0.03 | 0.03 | 0.03 |
| Silicon Antifoam | 0.01 | 0.01 | 0.01 | 0.01 | 0.01 |
| Blue dye | 25 ppm | 25 ppm | 25 ppm | 25 ppm | 25 ppm |
| Electrolyte | 0.20 | 0.20 | 0.20 | 0.20 | 0.20 |
| Perfume | 0.90 | 0.90 | 0.90 | 0.90 | 0.90 |
| Miscellaneous and water | Up to 100% | | | | |

EXAMPLE 3

The following fabric softener compositions were prepared according to the present invention :

| | A | B | C | D | E | F | G | H |
|---|---|---|---|---|---|---|---|---|
| DEQA | 2.6 | 2.6 | 2.6 | 2.6 | 19.0 | 19.0 | 19.0 | 19.0 |
| Fatty acid | 0.3 | 0.3 | 0.3 | 0.3 | — | — | — | — |
| Hydrochloride acid | 0.02 | 0.02 | 0.02 | 0.02 | 0.02 | 0.02 | 0.02 | 0.02 |
| ARP 1 | 0.02 | — | — | — | — | 0.1 | 0.23 | 0.2 |
| ARP 5 | — | 0.2 | 0.2 | — | — | — | — | 0.1 |
| ARP 3 | — | — | 0.2 | 0.05 | 0.3 | 0.2 | — | 0.2 |
| Perfume | 10 | 1.0 | 1.0 | 1.0 | 1.0 | 1.0 | 1.0 | 1.0 |
| PEI | — | 0.5 | 0.3 | 0.3 | — | 2.0 | 1.5 | 1.5 |
| HEDP | — | — | 0.05 | 0.05 | — | — | 0.3 | 0.3 |
| Silicone antifoam | 0.01 | 0.01 | 0.01 | 0.01 | 0.01 | 0.01 | 0.01 | 0.01 |
| Electrolyte | — | — | — | — | 0.1 | 0.1 | 0.1 | 0.1 |
| Dye | 10 ppm | 10 ppm | 10 ppm | 10 ppm | 25 ppm | 25 ppm | 25 ppm | 25 ppm |
| Water and minors | 100% | 100% | 100% | 100% | 100% | 100% | 100% | 100% |

EXAMPLE 4

The following dryer added fabric conditioner compositions were prepared according to the present invention:

| | A | B | C | D | E | F | G |
|---|---|---|---|---|---|---|---|
| DEQA (2) | — | — | — | — | 51.8 | 51.8 | 51.8 |
| DTMAMS | — | — | 26.0 | 26.0 | — | — | — |
| SDASA | 70.0 | 70.0 | 42.0 | 42.0 | 40.2 | 40.2 | 40.2 |
| Neodol 45-13 | 13.0 | 13.0 | — | — | — | — | — |
| Ethanol | 1.0 | 1.0 | — | — | — | — | — |
| ARP 1 (es) | 0.1 | — | — | 0.1 | 0.2 | — | — |
| ARP 2 (ec) | — | 0.1 | — | — | — | — | — |
| ARP 3 (es) | — | — | 0.05 | — | — | 0.2 | — |
| ARP 5 (d) | — | — | — | — | — | — | 0.3 |
| Perfume | 0.75 | 0.75 | 1.0 | 1.0 | 1.5 | 1.5 | 1.5 |
| Glycoperse S-20 | — | — | — | — | 15.4 | 15.4 | 15.4 |
| Glycerol monostearate | — | — | 26.0 | 26.0 | — | — | — |
| Digeranyl Succinate | 0.38 | 0.38 | — | — | — | — | — |
| Clay | — | — | 3.0 | 3.0 | — | — | — |
| Dye | 0.01 | 0.01 | — | — | — | — | — |

EXAMPLE 5

The following are non-limiting examples of pre-soak fabric conditioning and/or fabric enhancement compositions according to the present invention which can be suitably used in the laundry rinse cycle:

| Ingredients | A | B | C | D | E | F |
|---|---|---|---|---|---|---|
| Polymer | 3.5 | 3.5 | 3.5 | 3.5 | 3.5 | 3.5 |
| Dye fixative | 2.3 | 2.3 | 2.4 | 2.4 | 2.5 | 2.5 |
| Polyamine | 15.0 | 15.0 | 17.5 | 17.5 | 20.0 | 20.0 |
| Bayhibit AM | 1.0 | 1.0 | 1.0 | 1.0 | 1.0 | 1.0 |
| $C_{12}$–$C_{14}$ dimethyl hydroxyethyl quatemary ammonium chloride | — | 5.0 | 5.0 | — | — | — |
| Fabric softener active | — | — | 2.5 | 2.5 | — | — |
| Genamin C100 | 0.33 | — | 0.33 | 0.33 | 0.33 | — |
| Genapol V4463 | 0.2 | — | 0.2 | 0.2 | 0.2 | — |
| ARP1 | 1.0 | 2.0 | 0.1 | 0.5 | 0.05 | 0.08 |
| Water & minors | balance | balance | balance | balance | balance | balance |

EXAMPLE 6

The following are non-limiting examples of odor-absorbing compositions suitable for spray-on applications:

| Examples | A | B | C | D | E |
|---|---|---|---|---|---|
| Ingredients | Wt. % | Wt. % | Wt. % | Wt. % | Wt. % |
| HPBCD | 1.0 | — | 1.0 | — | 1.2 |
| RAMEB | — | 1.0 | — | 0.8 | — |
| Tetronic 901 | — | — | 0.1 | — | — |
| Silwet L-7604 | — | — | — | 0.1 | — |
| Silwet L-7600 | 0.1 | — | — | — | 0.1 |
| Bardac 2050 | — | — | — | 0.03 | — |
| Bardac 2250 | — | 0.2 | — | — | 0.1 |
| Diethylene glycol | — | 1.0 | — | — | 0.2 |
| Triethylene glycol | — | — | 0.1 | — | — |
| Ethanol | — | — | — | — | 2.5 |
| Perfume 1 | 0.1 | — | — | — | — |
| Perfume 2 | — | 0.05 | — | 0.1 | — |
| Perfume 3 | — | — | 0.1 | — | 0.1 |
| Kathon | 3 ppm | 3 ppm | 3 ppm | 3 ppm | — |
| HCl | to pH 4.5 | to pH 4.5 | to pH 3.5 | to pH 3.5 | to pH 3.5 |
| ARP1 | 5.0 | 1.0 | — | — | — |
| ARP3 | — | — | 0.5 | 0.1 | 0.08 |
| Distilled water | Bal. | Bal. | Bal. | Bal. | Bal. |

The perfume 1, 2, and 3 have the following compositions:

| Perfume | 1 | 2 | 3 |
|---|---|---|---|
| Perfume Ingredients | Wt. % | Wt. % | Wt. % |
| Anisic aldehyde | — | — | 2 |
| Benzophenone | 3 | 5 | — |
| Benzyl acetate | 10 | 15 | 5 |
| Benzyl salicylate | 5 | 20 | 5 |
| Cedrol | 2 | — | — |
| Citronellol | 10 | — | 5 |
| Coumarin | — | — | 5 |
| Cymal | — | — | 3 |
| Dihydromyrcenol | 10 | — | 5 |
| Flor acetate | 5 | — | 5 |
| Galaxolide | 10 | — | — |
| Lilial | 10 | 15 | 20 |
| Linalyl acetate | 4 | — | 5 |
| Linalool | 6 | 15 | 5 |
| Methyl dihydro jasmonate | 3 | 10 | 5 |
| Phenyl ethyl acetate | 2 | 5 | 1 |
| Phenyl ethyl alcohol | 15 | 15 | 20 |
| alpha-Terpineol | 5 | — | 8 |
| Vanillin | — | — | 1 |
| Total | 100 | 100 | 100 |

What is claimed is:

1. A perfume releasing compound, said compound is the reaction product of:

a) an amine having the formula:

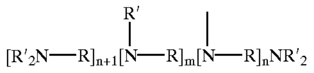

wherein R is $C_2$–$C_{12}$ alkylene, R' is hydrogen, m is from 2 to 700, n is from 0 to 350, m+n is at least 5, said amine having an Odor Intensity Index of less than a 1% solution of methyl anthranilate in dipropylene glycol;

b) an aldehyde perfume, a ketone perfume, and mixtures thereof;

wherein said perfume releasing compound has a Dry Surface Odor Index of more than 5.

2. A perfume releasing compound, said compound is the reaction product of:

a) an amine having the formula:

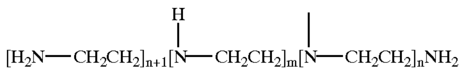

wherein the indices m and n are selected such that said polyethyleneimine has a molecular weight of from 150 to 2,000,000, said amine having an Odor Intensity Index of less than a 1% solution of methyl anthranilate in dipropylene glycol;

b) an aldehyde perfume, a ketone perfume, and mixtures thereof;

wherein said perfume releasing compound has a Dry Surface Odor Index of more than 5.

3. A compound according to claim 2 wherein said polyethyleneimine has a molecular weight of from 400 to 1,000,000.

4. A compound according to claim 3 wherein said polyethyleneimine has a molecular weight of from 5000 to 1,000,000.

5. A compound according to claim 2 wherein said aldehyde perfume has an Odor Detection Threshold less than or equal to 1 ppm.

6. A compound according to claim 2 wherein said aldehyde perfume comprises at least 5 carbon atoms.

7. A compound according to claim 2 wherein said aldehyde perfume is selected from the group consisting of ligustral, triplal, florhydral, Floralozone, cyclal C, 1-decanal, benzaldehyde, 2,4-dimethyl-3-cyclohexen-1-carboxaldehyde, 3,7-dimetyl-2,6-octadien-1-al, heliotropin, 2,4,6-trimethyl-3-cyclohexen-1-carboxaldehyde, 2,6-nonadienal, α-n-amyl cinnamic aldehyde, α-n-hexyl cinnamic aldehyde, P.T. Bucinal, lyral, cymal, methyl nonyl acetaldehyde, hexanal, trans-2-hexenal, burgeonal, and mixtures thereof.

8. A compound according to claim 2 wherein said aldehyde perfume has an Odor Detection Threshold less than or equal to 1 ppm.

9. A compound according to claim 2 wherein said aldehyde perfume comprises at least 5 carbon atoms.

10. A compound according to claim 2 wherein said ketone perfume is selected from the group consisting of α-damascone, β-damascone, δ-damascone, isodamascone, carvone, α-ionone, β-ionone, δ-ionone γ-methyl ionone, iso-E-Super, 2,4,4,7-tetramethyloct-6-en-3-one, benzyl acetone, damascenone, methyl dihydrojasmonate, methyl cedrylone, and mixtures thereof.

11. A perfume releasing compound comprising the reaction product of:

a) an amine having the formula:

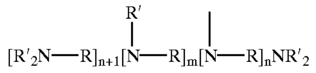

wherein R is $C_2$–$C_{12}$ alkylene, R' is hydrogen, m is from 2 to 700, n is from 0 to 350, m+n is at least 5, said amine having an Odor Intensity Index of less than a 1% solution of methyl anthranilate in dipropylene glycol;

b) an aldehyde perfume, a ketone perfume, and mixtures thereof, wherein said aldehyde and ketone has an Odor Detection Threshold less than or equal to 1 ppm;

wherein said compound has a Dry Surface Odor Index of more than 5.

12. A compound according to claim 11 wherein said perfume releasing compound comprises from 10% to 90% by weight, of an aldehyde or a ketone.

13. A compound according to claim 11 wherein the index m has the value from 4 to 400.

* * * * *